United States Patent [19]

Gleason et al.

[11] Patent Number: 4,937,253

[45] Date of Patent: Jun. 26, 1990

[54] ESTER PRODRUGS

[75] Inventors: John G. Gleason, Downingtown; Ralph F. Hall, Villanova; John F. Newton, West Chester, all of Pa.; Kathleen A. Phipps, Cherry Hill, N.J.; Joanne Smallheer, Berwyn, Pa.

[73] Assignee: SmithKline Beecham Corporation, Philadelphia, Pa.

[21] Appl. No.: 248,770

[22] Filed: Sep. 23, 1988

Related U.S. Application Data

[63] Continuation-in-part of Ser. No. 195,355, May 16, 1988, Pat. No. 4,820,719, which is a continuation of Ser. No. 926,314, Oct. 31, 1986, abandoned, which is a continuation-in-part of Ser. No. 848,608, Apr. 7, 1986, abandoned, which is a continuation-in-part of Ser. No. 725,264, Apr. 19, 1985, abandoned.

[51] Int. Cl.$^5$ .................... C07C 149/40; A61K 31/10
[52] U.S. Cl. ...................... 514/381; 514/533; 514/534; 548/253; 548/337; 549/549; 549/78; 549/502; 549/497; 560/15; 560/16
[58] Field of Search .................. 548/253, 337; 560/15, 560/16; 514/381, 533, 534; 549/549, 502, 497

[56] References Cited

U.S. PATENT DOCUMENTS 4,069,744  9/1986  Young et al. .................. 549/402

FOREIGN PATENT DOCUMENTS

| | | |
|---|---|---|
| 68739 | 1/1983 | European Pat. Off. . |
| 104885 | 4/1984 | European Pat. Off. . |
| 108592 | 5/1984 | European Pat. Off. . |
| 123543 | 10/1984 | European Pat. Off. . |
| 132366 | 1/1985 | European Pat. Off. . |
| 132367 | 1/1985 | European Pat. Off. . |
| 202759 | 11/1986 | European Pat. Off. . |
| 2746754 | 4/1978 | Fed. Rep. of Germany . |
| 2144422A | 3/1985 | United Kingdom . |

OTHER PUBLICATIONS

Gleason et al., *J. Med. Chem.* vol. 3, No. 6 (1987), pp. 959-961.
Derwent Patent Abstract 84-014267/03 of Japanese Patent Appln. 58206556A, published Dec. 1, 1983.
Derwent Patent Abstract 85-026589/05 of European Patent Appln. 132366A, published Jan. 30, 1985.
Chem. Abstract 96(17):143290n (1983).
Chem. Abstract 94(9): 64755y (1981).
Chemical Abstracts, vol. 96, 98909h (1982).
Chemical Abstracts, vol. 101, 151857g (1984).

*Primary Examiner*—Mary C. Lee
*Assistant Examiner*—M. S. Howard
*Attorney, Agent, or Firm*—James M. Kanagy; Stuart R. Suter; Edward T. Lentz

[57] ABSTRACT

This invention relates to ester prodrugs for alkanoic acid compounds useful as leukotriene antagonists, and pharmaceutical compositions containing such ester prodrug compounds. This invention also relates to methods of treating diseases in which leukotrienes are a factor by administration of an effective amount of the above compounds or compositions.

26 Claims, No Drawings

ESTER PRODRUGS

This is a continuation-in-part application of Ser. No. 195,355 filed May 16, 1988 now U.S. Pat. No. b 4,820,719, which is a continuation application of Ser. No. 926,314 filed Oct. 31, 1986 now abandoned, which is a continuation-in-part application of Ser. No. 848,608 filed Apr. 7, 1986 now abandoned, which is a continuation-in-part application of Ser. No. 725,264 filed Apr. 19, 1985, now abandoned.

BACKGROUND OF THE INVENTION

"Slow Reacting Substance of Anaphylaxis"(SRS-A) has been shown to be a highly potent bronchoconstricting substance which is released primarily from mast cells and basophils on antigenic challenge. SRS-A has been proposed as a primary mediator in human asthma. SRS-A, in addition to its pronounced effects on lung tissue, also produces permeability changes in skin and may be involved in acute cutaneous allergic reactions. Further, SRS-A has been shown to effect depression of ventricular contraction and potentiation of the cardiovascular effects of histamine.

The discovery of the naturally occurring leukotrienes and their relationship to SRS-A has reinforced interest in SRS-A and other arachidonate metabolites. SRS-A derived from mouse, rat, guinea pig and man have all been characterized as mixtures of leukotriene-$C_4$ (LTC$_4$), leukotriene-$D_4$ (LTD$_4$) and leukotriene-$E_4$ (LTE$_4$), the structural formulae of which are represented below.

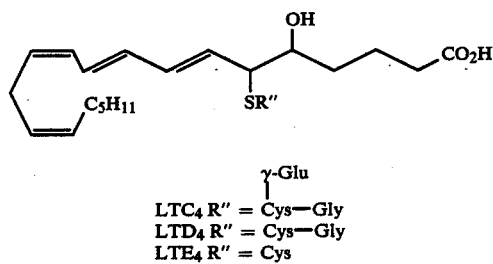

LTC$_4$ R" = Cys—Gly
LTD$_4$ R" = Cys—Gly
LTE$_4$ R" = Cys

Leukotrienes are a group of eicosanoids formed from arachidonic acid metabolism via the lipoxygenase pathway. These lipid derivatives originate from LTA$_4$ and are of two types: (1) those containing a sulfidopeptide side chain (LTC$_4$, LTD$_4$, and LTE$_4$), and (2) those that are nonpeptidic (LTB$_4$). Leukotrienes comprise a group of naturally occurring substances that have the potential to contribute significantly to the pathogenesis of a variety of inflammatory and ischemic disorders. The pathophysiological role of leukotrienes has been the focus of recent intensive studies.

As summarized by Lefer, A.M., *Biochemical Pharmacology*, 35, 2, 123–127 (1986) both the peptide and nonpeptide leukotrienes exert microcirculatory actions, promoting leakage of fluid across the capillary endothelial membrane in most types of vascular beds. LTB$_4$ has potent chemotactic actions and contributes to the recruitment and adherence of mobile scavenger cells to the endothelial membrane. LTC$_4$, LTD$_4$ and LTE$_4$ stimulate a variety of types of muscles. LTC$_4$ and LTD$_4$ are potent bronchoconstrictors and effective stimulators of vascular smooth muscle. This vasoconstrictor effect has been shown to occur in pulmonary, coronary, cerebral, renal, and mesenteric vasculatures.

Leukotrienes have been implicated in a number of pulmonary diseases. Leukotrienes are known to be potent bronchoconstrictors in humans. LTC and LTD have been shown to be potent and selective peripheral airway agonists, being more active than histamine. [See Drazen, J.M. et al., *Proc. Nat'l Acad. Sci. USA*, 77, 7, 4354–4358 (1980)]. LTC$_4$ and LTD$_4$ have been shown to increase the release of mucus from human airways in vitro. [See Marom, Z. et al., *Am. Rev. Respir. Dis.*, 126, 449–451 (1982).] The leukotriene antagonists of the present invention can be useful in the treatment of allergic or non-allergic bronchial asthma or pulmonary anaphylaxis.

The presence of leukotrienes in the sputum of patients having cystic fibrosis chronic bronchitis, and bronchiectasis at concentrations likely to have pathophysiological effects has been demonstrated by Zakrzewski et al. [See Zakrzewski, J. T. et al., Prostaglandins, 28, 5, 641 (1984).] Treatment of these diseases constitutes additional possible utility for leukotriene antagonists.

Leukotrienes have been identified in the nasal secretions of allergic subjects who underwent in vivo challenge with specific antigen. The release of the leukotrienes was correlated with typical allergic signs and symptoms. [See Creticos, P.S. et al., *New England J. of Med.*, 310, 25, 1626–1629 (1984).] This suggests that allergic rhinitis is another area of utility for leukotriene antagonists.

The role of leukotrienes and the specificity and selectivity of a particular leukotriene antagonist in an animal model of the adult respiratory distress syndrome was investigated by Snapper et al. [See Snapper, J.R. et al., *Abstracts of Int'l Conf. on Prostaglandins and Related Comp.*, Florence, Italy, p. 495 (June 1986).] Elevated concentrations of LTD$_4$ were shown in pulmonary edema fluid of patients with adult respiratory distress syndrome. [See Matthay, M. et al. *J. Clin. Immunol.*, 4, 79–483 (1984).] markedly elevated leukotriene concentrations have been shown in the edema fluid of a patient with pulmonary edema after cardiopulmonary bypass. [See Swerdlow, B.N., et al., *Anesth. Analg.*, 65, 306–308, (1986).] LTC and LTD have also been shown to have a direct systemic arterial hypotensive effect and produce vasoconstriction and increased vasopermeability. [See Drazen et al., ibid.] This suggests leukotriene antagonists can also be useful in the areas of adult respiratory distress syndrome, pulmonary edema, and hypertension.

Leukotrienes have also been directly or indirectly implicated in a variety of non-pulmonary diseases in the ocular, dermatologic, cardiovascular, renal, trauma, inflammatory, carcinogenic and other areas Further evidence of leukotrienes as mediators of allergic reactions is provided by the identification of leukotrienes in tear fluids from subjects following a conjunctival provocation test and in skin blister fluids after allergen challenge in allergic skin diseases and conjunctival mucosa. [See Bisgaard, H., et al., *Allergy*, 40, 417–423 (1985).] Leukotriene immunoreactivity has also been shown to be present in the aqueous humor of human patients with and without uveitis. The concentrations of leukotrienes were sufficiently high that these mediators were expected to contribute in a meaningful way to tissue responses. [See Parker, J.A. et al., *Arch Ophthalmol*, 104, 722–724 (1986).] It has also been demonstrated that psoriatic skin has elevated levels of leukotrienes. [See Ford-Hutchinson, *J. Allergy Clin. Immunol.*, 74, 437–440 (1984).] . Local effects of intracutaneous injections of synthetic leukotrienes in human skin were demonstrated by Soter et al. (See Soter et al., *J. Clin Invest Dermatol*, 80, 115–119 (1983).] Cutaneous vasodilation with edema formation and a neutrophil infiltrate were induced. Leukotriene synthesis inhibitors or leukotriene antagonists can also be useful in the treatment of ocular or dermatological diseases such as allergic conjunctivitis, uveitis, allergic dermatitis or psoriasis.

Another area of utility for leukotriene antagonists is in the treatment of cardiovascular diseases. Since peptide leukotrienes are potent coronary vasoconstrictors, they are implicated in a variety of cardiac disorders including arrhythmias, conduction blocks and cardiac depression. Synthetic leukotrienes have been shown to be powerful myocardial depressants, their effects consisting of a decrease in contractile force and coronary flow. The cardiac effects of $LTC_4$ and $LTD_4$ have been shown to be antagonized by a specific leukotriene antagonist, thus suggesting usefulness of leukotriene antagonists in the areas of myocardial depression and cardiac anaphylaxis. [See Burke, J.A., et al., *J. Pharmacology and Experimental Therapeutics*, 221, 1, 235–241 (1982).]

$LTC_4$ and $LTD_4$ have been measured in the body fluids of rats in endotoxic shock, but are rapidly cleared from the blood into the bile. Thus leukotrienes are formed in ischemia and shock. Specific inhibitors of leukotriene biosynthesis reduce the level of leukotrienes and therefore reduce manifestations of traumatic shock, endotoxic shock, and acute myocardial ischemia. Leukotriene receptor antagonists have also been shown to reduce manifestations of endotoxic shock and to reduce extension of infarct size. Administration of peptide leukotrienes has been shown to produce significant ischemia or shock. [See Lefer, A.M., *Biochemical Pharmacology*, 35, 2, 123–127 (1986).] Thus further areas of utility for leukotriene antagonists can be the treatment of myocardial ischemia, acute myocardial infarction, salvage of ischemic myocardium, angina, cardiac arrhythmias, shock and atherosclerosis.

Leukotriene antagonists can also be useful in the area of renal ischemia or renal failure. Badr et al. have shown that $LTC_4$ produces significant elevation of mean arterial pressure and reductions in cardiac output and renal blood flow, and that such effects can be abolished by a specific leukotriene antagonist. [See Badr, K.F. et al., *Circulation Research*, 54, 5, 492–499 (1984). Leukotrienes have also been shown to have a role in endotoxin-induced renal failure and the effects of the leukotrienes selectively antagonized in this model of renal injury. [See Badr, K.F., et al., *Kidney International*, 30, 474–480 (1986).] $LTD_4$ has been shown to produce local glomerular constrictor actions which are prevented by treatment with a leukotriene antagonist. [See Badr, K.F. et al., *Kidney International*, 29, 1, 328 (1986). $LTC_4$ has been demonstrated to contract rat glomerular mesangial cells in culture and thereby effect intraglomerular actions to reduce filtration surface area. [See Dunn, M.J. et al., *Kidney International*, 27, 1, 256 (1985). Thus another area of utility for leukotriene antagonists can be in the treatment of glomerulonephritis.

Leukotrienes have also been indicated in the area of transplant rejection. An increase in cardiac and renal allograft survival in the presence of a leukotriene receptor antagonist was documented by Foegh et al. [See Foegh, M.L. et al. *Advances in Prostaglandin, Thromboxane, and Leukotriene Research*, 13, 209–217 (1985).] Rejection of rat renal allografts was shown to produce increased amounts of $LTC_4$.[See Coffman, T.M. et al., *Kidney International*, 29, 1, 332 (1986).

A further area of utility for leukotriene antagonists can be in treatment of tissue trauma, burns, or fractures. A significant increase in the production of cysteinyl leukotrienes was shown after mechanical or thermal trauma sufficient to induce tissue edema and circulatory and respiratory dysfunction. [See Denzlinger, C. et al., *Science*, 230, 330–332 (1985).]

Leukotrienes have also been shown to have a role in acute inflammatory actions. $LTC_4$ and $LTD_4$ have potent effects on vascular caliber and permeability and $LTB_4$ increases leukocyte adhesion to the endothelium. The arteriolar constriction, plasma leakage, and leukocyte adhesion bear close resemblence to the early events in acute inflammatory reactions. [See Dahlen, S.E. et al., *Proc. Natl. Acad. Sci. USA*, 78, 6, 3887–3891 (1981).] Mediation of local homeostasis and inflammation by leukotrienes and other mast cell-dependent compounds was also investigated by Lewis et al. [See Lewis, R.A. et al., *Nature*, 293, 103–108 (1981). Leukotriene antagonists can therefore be useful in the treatment of inflammatory diseases including rheumatoid arthritis and gout.

Cysteinyl leukotrienes have also been shown to undergo enterohepatic circulation, and thus are indicated in the area of inflammatory liver disease. [See Denzlinger, C. et al., *Prostaglandins Leukotrienes and Medicine.* 21, 321–322 (1986).] Leukotrienes can also be important mediators of inflammation in inflammatory bowel disease. [See Peskar, B.M. et al., *Agents and Actions*, 18, 381–383 (1986).] Leukotriene antagonists thus can be useful in the treatment of inflammatory liver and bowel disease.

Leukotrienes have been shown to modulate IL-1 production by human monocytes. [See Rola-Pleszczynski, M. et al., *J. of Immun.*, 135, 6, 3958–3961 (1985). This suggests that leukotriene antagonists may play a role in IL-1 mediated functions of monocytes in inflammation and immune reactions.

$LTA_4$ has been shown to be a factor in inducing carcinogenic tumors and is considered a link between acute immunologic defense reactions and carcinogenesis. Leukotriene antagonists can therefore possibly have utility in treatment of some types of carcinogenic tumors. [See Wischnewsky, G.G. et al. *Anticancer Res.* 5, 6, 639 (1985).]

Leukotrienes have been implicated in gastric cytodestruction and gastric ulcers. Damage of gastro intestinal mucosa because of potent vasoconstriction and stasis of blood flow is correlated with increased levels of $LTC_4$. Functional antagonism of leukotriene effects may represent an alternative in treatment of mucosal injury. [See Dreyling, K.W. et al., *British J. Pharmacology*, 88, 236P (1986), and Peskar, B.M. et al. *Prostaglandins*, 31, 2, 283–293 (1986).] A leukotriene antagonist has been shown to protect against stress-induced gastric ulcers in rats. [See Ogle, C.W. et al., *IRCS Med. Sci.*, 14, 114–115 (1986).]

Other areas in which leukotriene antagonists can have utility because leukotrienes are indicated as mediators include prevention of premature labor [See Clayton, J.K. et al., *Proceedings of the BPS*, 573P, 17–19 Dec. 1984]; treatment of migraine headaches [See Gazzaniga, P.P. et al., *Abstracts Int'l Conf. on Prostaglandins and*

Related Comp., 121, Florence, Italy (June 1986)]; and treatment of gallstones [See Doty, J.E. et al., *Amer. J. of Surgery*, 145, 54–61 (1983) and Marom, Z et al., *Amer. Rev. Respir. Dis.*, 126, 449–451 (1982).

By antagonizing the effects of $LTC_4$, $LTD_4$ and $LTE_4$ or other pharmacologically active mediators at the end organ, for example airway smooth muscle, compounds and pharmaceutical compositions which act as leukotriene antagonists are valuable in the treatment of diseases in subjects, including human or animals, in which leukotrienes are a key factor. This invention relates to ester prodrugs of selected chemical compounds and pharmaceutical compositions containing such prodrugs which are useful in treating diseases in which leukotrienes are a factor.

DETAILED DESCRIPTION OF THE INVENTION

The ester prodrugs of this invention are represented by the following general structural formula (I)

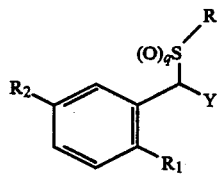

wherein (a) $R_1$ is $C_8$ to $C_{13}$ alkyl, $C_7$ to $C_{12}$ alkoxy, $C_7$ to $C_{12}$ alkylthio, $C_{10}$ to $C_{12}$ 1-alkynyl, 10-undecynyloxy, 11-dodecynyl, phenyl $C_4$ to $C_{10}$ alkyl, phenyl-C3 to C9 alkoxy, phenylthio-C3 to C9 alkyl with the phenyl optionally mono substituted with bromo, chloro, trifluoromethyl, $C_1$ to $C_4$ alkoxy, methylthio or trifluoromethylthio, furyl-C4 to $C_{10}$ alkyl, trifluoromethyl-C7 to $C_{12}$ alkyl or cyclohexyl-C4 to $C_{10}$ alkyl; and $R_2$ is hydrogen, bromo, chloro, methyl, trifluoromethyl, hydroxy, $C_1$ to $C_4$ alkoxy or nitro; or (b) $R_1$ is hydrogen and $R_2$ is $C_8$ to $C_{13}$ alkyl, $C_7$ to $C_{12}$ alkoxy, $C_7$ to $C_{12}$ alkylthio, $C_{10}$ to $C_{12}$ 1-alkynyl, 10-undecynyloxy, 11-dodecynyl, phenyl-C4 to $C_{10}$ alkyl, phenyl-C3 to C9 alkoxy, phenylthio-C3 to C9 alkyl with the phenyl optionally mono substituted with bromo, chloro, trifluoromethyl, $C_1$ to $C_4$ alkoxy, methylthio or trifluoromethylthio, furyl-C4 to $C_{10}$ alkyl, trifluoromethyl-C7 to $C_{12}$ alkyl or cyclohexyl-C4 to $C_{10}$ alkyl;

q is 0, 1 or 2; Y is $COR_3$,

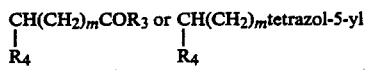

wherein the tetrazol-5-yl is unsubstituted or substituted with A;

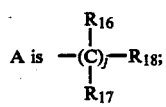

$R_{16}$ and $R_{17}$ are independently hydrogen or $C_{1-4}$ alkyl, j is 0 to 6;

$R_{18}$ is hydrogen, $C_{1-4}$ alkyl, $COR_3$, $SO_3H$, $SO_2H$, $SO_2NH_2$, $COCH_2OH$ or $CHOHCH_2OH$;

$R_3$ is amino, $(CH_2)_nCO_2CH_2CONR_{16}R_{17}$, or $OR_{14}$;

$R_{14}$ is hydrogen, $C_1$ to $C_6$ alkyl, cycloalkyl, aryl, arylalkyl, alkylaryl, alkylarylalkyl, alkyl substituted amino or alkylamino, indanyl, pivaloyloxymethyl, acetoxymethyl, propionyloxymethyl, glycyloxymethyl, phenylglycyloxymethyl or thienylglycyloxymethyl;

$R_4$ is hydrogen, methyl, $C_1$ to $C_4$ alkoxy, fluoro or hydroxy;

m is 0, or 1;

R is

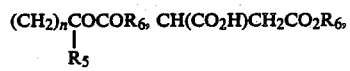

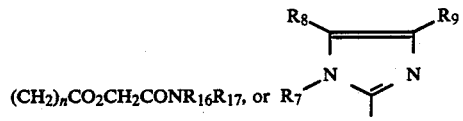

n is 0 to 6;

$R_5$ is hydrogen, amino, or $NHCOCH_2CH_2CH(NH_2)CO_2H$;

$R_6$ is amino, $NH(CH_2)_nCO_2H$, $SO_3H$, $SO_2NH_2$, CN, tetrazol-5-yl unsubstituted or substituted with A as defined above, or $OR_{15}$;

$R_7$ is hydrogen, $C_1$ to $C_4$ alkyl or $C_3$ to $C_4$ alkenyl;

$R_8$ is hydrogen, $C_1$ to $C_4$ alkyl, carboxyl or carboxamido, or, when $R_7$ and $R_9$ are hydrogen or $C_1$ to $C_4$ alkyl,

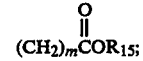

$R_9$ is hydrogen, $C_1$ to $C_6$ alkyl or

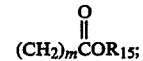

$R_{15}$ is hydrogen, $C_1$ to $C_6$ alkyl, cycloalkyl, aryl, arylalkyl, alkylaryl, alkylarylalkyl, alkyl substituted amino or alkylamino, indanyl, pivaloyloxymethyl, acetoxymethyl, propionyloxymethyl, glycyloxymethyl, phenylglycyloxymethyl or thienylglycyloxymethyl;

provided that (1) when n is 0, $R_5$ is hydrogen, (2) $R_7$, $R_8$ and $R_9$ are not all hydrogen, (3) any of $R_1$ and $R_2$ are not alkylthio or phenylthioalkyl when q is 1 or 2; (4) $R_3$ and $R_6$ are not both hydroxy (5) $OR_{14}$ and $OR_{15}$ are not simultaneously hydroxy or (6) if $R_4$ is hydroxy and m is 0, $R_{14}$ is hydrogen; or a pharmaceutically acceptable salt thereof.

The term phenylthioalkyl is used herein to mean

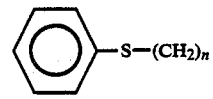

The prodrug compounds of this invention comprise both mono- and diesters. Specifically monoesters wherein the ester group is located at the R or at the Y position, or diester compounds wherein ester groups occur at both the R and Y positions of formula (I) are within the present invention. However, if the Y chain contains a hydroxy group at the $R_4$ position and m is 0, only monoesters or diesters wherein the ester group is located at the R position are within the scope of the invention.

A particular class of compounds of this invention are the hydroxy substituted monoester compounds having the ester group at the R position represented by structural formulae (IIA) and (IIB)

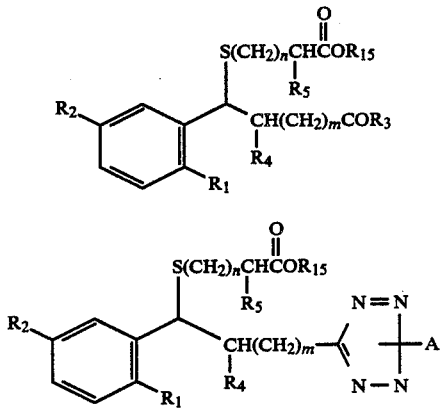

wherein $R_1$, $R_2$, $R_5$, m, and n are described above; $R_3$ is amino or OH; $R_4$ is hydroxy; and $R_{15}$ is other than hydrogen.

The compounds of formulae (IIA) and (IIB) are exemplified by the following compounds:
(1) 2-hydroxy-3-[(2-carboisopropoxyethyl)thio]-3-[2-(8-phenyloctyl)]propanoic acid;
(2) 2-hydroxy-3-[(2-carbocyclopentoxyethyl)thio-3-[2-(8-phenyloctyl)phenyl]propanoic acid;
(3) 2-hydroxy-3-[(2-carboethoxyethyl)thio]-3-[2-(8-phenyloctyl)phenyl]propanoic acid;
(4) 2-hydroxy-3-[(2-carbomethoxyethyl)thio]-3-[2-(8-phenyloctyl)phenyl]propanoic acid;
(5) 2(S)-hydroxy-3(R)-[(2-carboisopropoxyethyl)thio]-3-[2-(8-phenyloctyl)phenyl]propanoic acid;
(6) 2(S)-hydroxy-3(R)-[(2-carboethoxyethyl)thio]-3-[2-(8-phenyloctyl)phenyl]propanoic acid; or
(7) 5-[l(R,S)-hydroxy-2(S,R)-(2-carbomethoxyethylthio)]-2-[2-(8-phenyloctyl)phenyl]ethyl tetrazole.
(8) 2-hydroxy-3-[(diethylaminocarbonyl)methoxy (2-carbonylethylthio)]-3-[2-(8-phenyloctyl)phenyl]propanoic acid; or
(9) 3-[2-(2-dimethylaminoethoxycarbonylethyl)thio]-2-hydroxy-3-[2-(8-phenyloctyl)phenyl]propanoic acid.

A second class of compounds of this invention are monoesters having the ester group at the R position represented by the structural formula (III).

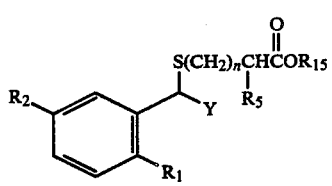

wherein $R_1$, $R_2$, $R_5$, and n are described above as in Formula (I); Y is as described above provided that $R_4$ is other than hydroxy and $R_{14}$ is hydrogen; and $R_{15}$ is other than hydrogen as described above.

The compounds of the formula (III) are exemplified by the following compounds:

(1) methyl 4-thia-5-(2-dodecylphenyl-5-(tetrazol-5-yl)pentanoate;
(2) 3-(2-carbomethoxyethylthio)-3-[2-(8-phenyloctyl)-phenyl]propanoic acid;
(3) methyl 4-thia-5-(2-dodecylphenyl)-5-carboxamidopentanoate; or
(4) methyl 4-thia-5-(2-dodecylphenyl)-6-(tetrazol-5-yl)hexanoate.

A third particular class of compounds of this invention are the monoester compounds having the ester group at the Y position represented by the structural formula (IVA) and (IVB):

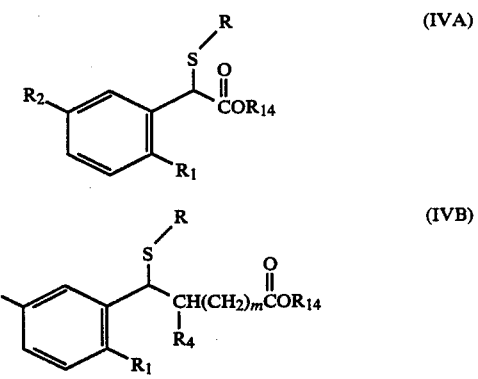

wherein $R_1$, $R_2$, and m are described above as in Formula (I); $R_4$ is hydrogen, methyl, fluoro and $C_1$ to $C_4$ alkoxy when m is 0 or $R_4$ is hydrogen, methyl, fluoro, $C_1$ to $C_4$ alkoxy or hydroxy when m is 1; R is as described above provided that $R_{15}$ is hydrogen; and $R_{14}$ is other than hydrogen as defined above.

The compounds of formula (IV) are exemplified by the following compounds:
(1) t-butyl 3-(2-carboxyethylthio)-3-(2-dodecylphenyl)-propionate;
(2) methyl 2-methyl-3-(2-carboxyethylthio)-3-(2-(dodecylphenyl)propanoate;
(3) t-butyl 3-(2-carboxyethylthio)-3-[2-(8-phenyloctyl)-5-trifluoromethylphenyl]propanoate;
(4) methyl 2-(2-carboxypropylthio)-2-(2-dodecylphenyl)acetate;
(5) methyl 2-(2-carboxamidoethylthio)-2-(2-dodecylphenyl)acetate;
(6) methyl 2-(2-dodecylphenyl)-5-sulfo-3-thiapentanoate;
(7) methyl 2-(2-sulfonamidoethylthio)-2-(2-dodecylphenyl)acetate;
(8) methyl 2-(2-cyanoethylthio)-2-(2-dodecylphenyl)acetate; or
(9) 5-carbomethoxy-5-(2-dodecylphenyl)-3-carboxy-4-thiapentanoic acid.

A further class of compounds of this invention are diester compounds represented by the following general structural formulae (VA), (VB), and (VC):

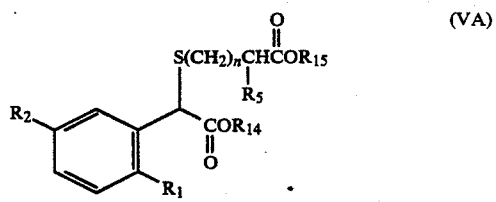

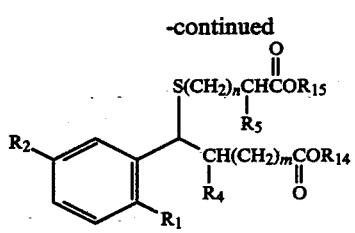

(VB)

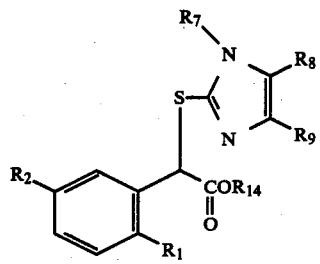

(VC)

wherein $R_1$, $R_2$, $R_5$, $R_7$, $R_8$, $R_9$, n and m are as described above in Formula (I); $R_4$ is hydrogen, methyl, fluoro or $C_1$ to $C_4$ alkoxy when m is 0, or $R_4$ is hydrogen, methyl, fluoro, $C_1$ to $C_4$ alkoxy or hydroxy when m is 1; one of $R_8$ or $R_9$ is

and $R_{14}$ and $R_{15}$ are other than hydrogen as described above.

The compounds of formula (VA), (VB) and (VC) are exemplified by the following compounds:

(1) methyl-3-[(2-carbomethoxyethyl)thio]-3-[2-(8-phenyloctyl)phenyl]propanoate;

(2) methyl-3(S)-[(2-carbomethoxyethyl)thio]-3-[2-(8-phenyloctyl)phenyl]propanoate;

(3) di-(t-butyl)-3-aza-4-oxo-7-thia-8-(2-dodecylphenyl)-decanedioate;

(4) methyl 2-(2-dodecylphenyl)-2-(1,4-dimethyl-5-carbethoxy-2-imidazolylthio)acetate;

(5) methyl 2-(2-dodecylphenyl)-2-(1-methyl-4-propyl-5-carbethoxy-2-imidazolylthio)acetate;

(6) methyl 2-(carbomethoxymethylthio)-2-(2-dodecylphenyl)acetate;

(7) methyl 2-(2-carbomethoxyethylthio)-2-(2-dodecylphenyl)acetate;

(8) 3-aza-4-oxo-7-thia-8-(2-dodecylphenyl)-nonanedioic acid dimethyl ester; or (9) methyl 2-(2-carbomethoxyethylthio)-2-[2-(8-phenyloctyl)phenyl]acetate.

Some of the compounds of the formula (I) contain two asymmetric centers. This leads to the possibility of four stereoisomers for each such compound. In practice, these compounds are prepared as a mixture of two stereoisomers. Resolution procedures employing, for example, optically active amines furnish the separated enantiomers. The compounds of the present invention include all stereoisomers or enantiomers of formula (I).

The compounds of the present invention, depending on their structure, are capable of forming salts with pharmaceutically acceptable acids and bases, according to procedures well known in the art. Such acceptable acids include inorganic and organic acids, such as hydrochloric, sulfuric, methanesulfonic, benzenesulfonic, p-toluenesulfonic and acetic acid. Such acceptable bases include organic and inorganic bases, such as ammonia, arginine, organic amines, alkali metal bases, alkaline earth metal bases and transition metal bases. Of particular utility are the potassium, zinc, sodium, magnesium, ammonium, calcium, ethylene diamine, or piperazine salts of the ester or diester compounds of formula (I).

The compounds of formula (I) wherein Y is $COR_3$ are conveniently prepared from an aldehyde precursor of the following structural formula (VIII)

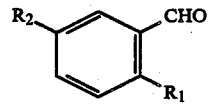

(VIII)

wherein $R_1$ and $R_2$ are described above. A compound of formula (VIII) is treated with trimethylsilyl cyanide in the presence of zinc iodide at low temperatures in an inert solvent to form the trimethylsilyl-protected cyanohydrin. Treatment of this with gaseous hydrogen chloride in methanol provides the methyl 2-hydroxyacetate derivative which is converted to the 2-chloroacetate with thionyl chloride. This valuable intermediate is then reacted with a substituted thiol selected to give a product of formula (I).

The compounds of formula (I) wherein Y is $CH_2COR_3$ are prepared by reacting the appropriate aldehyde of the formula (VIII) and an esterified bromoacetate, conveniently t-butyl bromoacetate, with a mixture of diethyl aluminum chloride, zinc dust and a catalytic amount of cuprous bromide at low temperatures in an inert solvent to give the esterified 3-hydroxypropionate derivative. The 3-hydroxypropionate derivative can also be prepared by the reaction of a suitable ester enolate with the appropriate aldehyde of formula (VIII). This derivative is reacted directly with a substituted thiol in trifluoroacetic acid. Alternatively, a mixture of trimethyl borate and zinc in tetrahydrofuran may be used to prepare the 3-hydroxypropionate derivative. By employing an esterified 2-bromopropionate in the above reaction with an aldehyde (VIII), the sulfide compounds wherein Y is $CH(CH_3)COR_3$ are obtained.

To prepare the desired compounds of formula (I) wherein q is 1 or 2, the appropriate thio product is conveniently oxidized with sodium periodate or meta-chloroperbenzoic acid to obtain the sulfoxide or sulfone product.

The aldehydes of formula (VIII) are known or readily prepared utilizing the general procedures described as follows.

The aldehyde precursors to the compounds of formula (I) wherein $R_1$ is, for example, an alkyl radical containing 8 to 13 carbon atoms are prepared from the appropriate 2-methoxyphenyl-4,4-dimethyloxazoline [see Meyers et al. *J. Org. Chem.*, 43 1372 (1978)].

The aldehyde precursors of the compounds of formula (I) wherein $R_1$ is, for example, an alkoxy radical containing 7 to 12 carbon atoms are prepared by the O-alkylation of the appropriate 2-hydroxybenzaldehyde with the corresponding alkylating agent.

The aldehyde precursors to the compounds of formula (I) wherein $R_1$ is a 1-alkynyl radical containing 10 to 12 carbon atoms are prepared by coupling a 2-halobenzaldehyde with the appropriate 1-alkyne in the presence of cuprous iodide and $(P_3)_2PdCl_2$. [See Hagihara, et al. *Synthesis*, 627, (1980)]. The catalytic hydrogenation of these alkynyl containing precursors under standard conditions affords the aldehyde precursors of the compounds of the formula (I) wherein $R_1$ is an alkyl or phenylalkyl radical.

The alkylthio containing aldehyde precursors of the compounds of formula (I) are prepared by the reaction of the appropriately substituted halo alkylthio benzene with magnesium and dimethylformamide.

The phenylthioalkyl containing aldehyde precursors of the compounds of formula (I) are prepared by the reaction of the appropriately substituted haloalkyl benzaldehyde with a thiophenol and triethylamine.

Alternatively, the compounds of formula (I) having an ester group at the R position wherein Y is $CH_2COR_3$ or $CH_2CO_2H$ are prepared from a propenoate precursor of the following structural formula (IX)

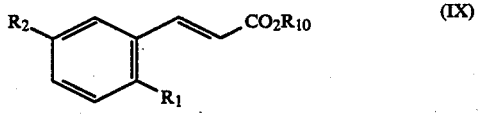

wherein $R_1$ and $R_2$ are described above, and $R_{10}$ is hydrogen or a carboxylic acid or ester protective group. Compounds of formula (IX) having $R_{10}$ as an ester protective group are used to prepare compounds of formula I having an ester group at the Y position or at the Y and R positions simultaneously. A compound of formula (IX) is reacted with a mixture of alkali metal alkoxide, such as sodium methoxide, and substituted thiol to give, after optional removal of the protective group, products of formula (I).

The propenoate precursors of formula (IX) are prepared from the corresponding aldehydes of formula (VIII) by general procedures such as reaction with an alkyl (triphenylphosphoranylidene)acetate or by conversion of the aldehyde to a 3-hydroxypropionate derivative, as described above, followed by an elimination reaction to form the double bond. Additionally, the propionate precursor is obtained from a 3-methanesulfonyloxypropionate derivative by treatment with triethylamine.

The diester compounds, or the monoesters having the ester group at the Y position of formula (I) wherein Y is $CH(OH)(CH_2)_mCOR_3$ are prepared from an epoxide precursor of the following structural formula (X)

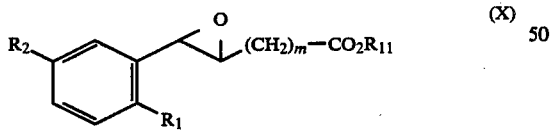

wherein $R_1$, $R_2$ and m are described above, and $R_{11}$ is lower alkyl, such as methyl or ethyl. The monoester compounds of formula (I) having the ester group at the R position are prepared from a compound of formula (X) wherein $R_{11}$ is hydrogen or a carbocylic acid protective group. A compound of formula (X) is reacted in an inert solvent with triethylamine and a substituted thiol selected to give, after optional removal of protective groups, a product of formula (I).

Alternatively for monoesters having the ester group at the R position of formula (I) a compound of formula (X) is reacted in an inert solvent with a substituted thiol to yield a diacid compound of formula (XI) represented by the following structural formula

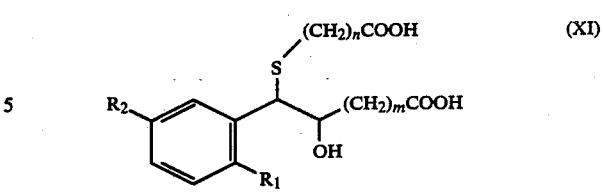

wherein $R_1$, $R_2$, m and n are defined as for formula (I). A protecting group is then added to the carboxylic acid moiety terminating the chain containing the hydroxy group. For example, the formula (XI) compound can be treated with a diazomethane in an inert organic solvent such as toluene. The carboxylic acid group on the sulfur-containing chain is then esterified by an appropriate esterification reaction commonly known in the art, such as treating it with a haloacetamide or alkylating agent. The protecting group is then removed by commonly known reactions, such as by reaction with trifluoroacetic acid, to yield the desired monoester.

Monoesters of formula (I) wherein the ester group is at either the Y or R positions can also be prepared from diacid compounds of formula (XI) by treating the diacid with an appropriate alcohol in the presence of an acid. Diesters of formula (I) can be prepared using this process by running the reaction under more rigorous conditions, such as at a higher temperature or for a longer time period.

The epoxide precursors of formula (X) where m is 0 are prepared by reaction of an aldehyde of the formula (VIII) with a lower alkyl chloroacetate and an alkali metal alkoxide such as sodium methoxide.

Alternatively, the compounds of the formula (I) wherein Y is $CH(OH)COR_3$ are prepared from a propenoate precursor of formula (IX) wherein $R_{10}$ is lower alkyl.

The compounds of Formula (I) of known chirality can be prepared by reacting a compound of formula (XIV) with a strong base to generate a thiol which is then reacted with an alkylating agent or Michael acceptor to yield the desired compound.

A compound of Formula (XIV) is represented by the following structure:

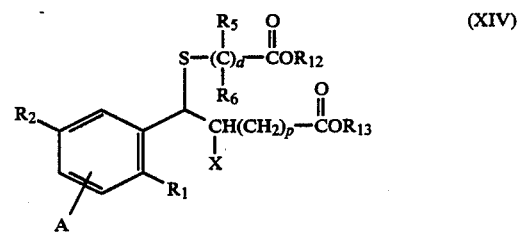

wherein
d is 2;
X is OH; p is 0 or 1;
one of $R_5$ or $R_6$ adjacent to the ester group is H or $C_{1-4}$alkyl; and
$R_1$ and $R_2$, are as defined in Formula (I) and $R_{12}$ and $R_{13}$ are independently selected from hydrogen or $C_{1-6}$ alkyl. Suitable strong bases include those such as sodium methoxide, sodium hydride, sodium amide, lithium diisopropyl amide or others. The reaction is conducted in an aprotic solvent such as tetrahydrofuran, dimethylsulfoxide, or N,N-dimethylformamide at ambient temperature and pressure. The resulting intermediate thiol of known chirality is represented by Formula (XV)

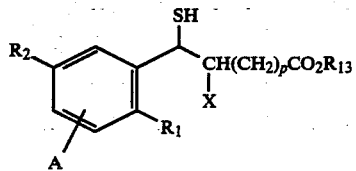

wherein $R_1$, $R_2$, $R_{13}$, A, X, and p are as defined in Formula (XIV).

The thiol of Formula (XV) is reacted with an alkylating agent or Michael acceptor to yield a compound of Formula (I). Suitable alkylating agents include alkyl halides such as an appropriately substituted alkyl halide, for example bromide or iodide. The reaction is conducted in an aprotic solvent at ambient temperature and pressure. Suitable Michael acceptors include compounds which undergo nucleophilic addition. Examples include compounds containing carbonyl, carboalkoxy, or cyano groups conjugated with a double or triple bond. Carbonyl compounds or alkynes represented by the following structural formulae are especially suitable

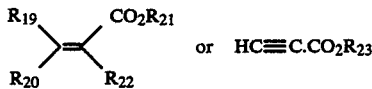

wherein $R_{19}$, $R_{20}$, and $R_{22}$ are independently selected from hydrogen or $C_{1-6}$alkyl. $R_{21}$ and $R_{23}$ are independently selected from H, aryl, or $C_{1-6}$alkyl. The reaction is conducted in an aprotic solvent at ambient temperature and pressure.

Appropriate modifications of the general processes disclosed, and as further described in the Examples provided hereinbelow, furnish the various compounds defined by formula (I).

The rate of hydrolysis of the claimed prodrugs to the derivative compounds was determined in 50% guinea pig plasma using the following method. Fresh guinea pig plasma was obtained each day prior to experimentation. Duplicate incubations were prepared containing 1.5 mls guinea pig plasma, 1.5 mls TRIS buffer, pH 7.4 and either 100 or 500 µM concentration of one of the test compounds. The tubes were incubated at 37° C. along with appropriate blanks. One hundred µL aliquots were removed from the incubations at 1,2,4,6,8,10,15,30,60 and 420 minutes into the incubation. Aliquots were prepared for high pressure liquid chromatography, (HPLC) analysis in the following manner. Internal standard, [3(S)-[(2-carboxyethyl)thio]-3-[2-(8-phenyloctyl)phenyl]2(S)-methoxypropionic acid, was added to each aliquot along with 400 µL of methyl formate containing 0.5% TFA. Aliquots were vortexed and spun for 2 minutes at 2500 rpm. The organic layer was removed and transferred to another tube. The extraction was repeated and the extracts were combined and evaporated under nitrogen. The evaporated samples were redissolved in 100 µL mobile phase for analysis and 25 µL of each sample was injected into the liquid chromatograph. Concentrations of the hydrolyzed metabolite, 3-[(2-carboxyethyl)thio]-3-[2-(8-phenyloctyl)phenyl]-2-hydroxypropanoic acid were quantitated by HPLC from standard curves of the synthetic sodium salt of this compound dissolved in guinea pig plasma.

The half-time of the hydrolysis of the compounds being tested to the above standard was determined by plotting a graph of product formation, or µg/ml standard v. time in minutes. The half-time was determined graphically as the time when product formation was one-half of the maximal product formation in the assay. The half-times of the hydrolysis are summarized in the following table.

TABLE I

![structure: phenyl ring with S-R group, Y group, and (CH2)8-phenyl substituent]

| R | Y | t ½ (minutes)* |
|---|---|---|
| $(CH_2)_2CO_2CH_3$ | $CH(OH)CO_2H$ | 11 |
| $(CH_2)_2CO_2CH_2CH_3$ | $CH(OH)CO_2H$ | 7 |
| $(CH_2)_2CO_2CH(CH_3)_2$ | $CH(OH)CO_2H$ | 5 |
| $(CH_2)_2CO_2$-cyclopentyl | $CH(OH)CO_2H$ | 6 |
| $(CH_2)_2CO_2CH_2CON(CH_2CH_3)_2$ | $CH(OH)CO_2H$ | 7 |
| $(CH_2)_2CO_2CH_2CON(CH_2CH_3)_2$ | $CH(OH)CO_2CH_2N(CH_2CH_3)_2$ | >420 |
| $(CH_2)_2CO_2H$ | $CH(OH)CO_2CH_3$ | >420 |
| $(CH_2)_2CO_2CH_3$ | $CH(OH)CO_2CH_3$ | >420 |

*Half life of conversion of ester to acid in guinea pig serum.

The compounds of formula (I) of the present invention act as prodrugs of their acid derivatives which are active as leukotriene antagonists. In those prodrug compounds of formula (I) wherein $R_4$ is hydroxy and m is 0 and an ester group is present at the R position as in the formula (IIA) and (IIB), the ester will readily hydrolize in guinea pig plasma to form the acid. All compounds of this class hydrolyzed at similar rates with half-times of hydrolysis of 5 to 11 minutes. If the ester group is present at the Y position of formula (I) and $R_4$ is hydroxy, the acids are not readily formed within the experimental period (7 hours). For diester compounds of formula (I) wherein $R_4$ is hydroxy having ester groups at both the R and Y positions, the monoester having the ester group at the Y position is formed, and the acids are therefore not readily formed. For prodrug compounds of formula (I) wherein $R_4$ is not hydroxy, the esters cleave at both the Y and R positions to form the active acid compounds. Thus monoesters at the Y position, monoesters at the R position, and diesters for these non-hydroxy prodrug compounds yield active acid derivatives.

Pharmaceutical compositions of the present invention comprise a pharmaceutical carrier or diluent and an amount of a prodrug compound of the formula (I) or a pharmaceutically acceptable salt, such as an alkali metal salt thereof, sufficient to produce the inhibition of the effects of leukotrienes.

When the pharmaceutical composition is employed in the form of a solution or suspension, examples of appropriate pharmaceutical carriers or diluents include: for aqueous systems, water; for non-aqueous systems, ethanol, glycerin, propylene glycol, corn oil, cottonseed oil, peanut oil, sesame oil, liquid parafins and mixtures thereof with water; for solid systems, lactose, kaolin and mannitol; and for aerosol systems, dichlorodifluoromethane, chlorotrifluoroethane, compressed carbon dioxide or other suitable propellants. Also, in addition to the pharmaceutical carrier or diluent, the instant compositions may include other ingredients such as stabilizers, antioxidants, preservatives, lubricants, suspending agents, viscosity modifiers and the like, provided that the additional ingredients do not have a detrimental effect on the therapeutic action of the instant compositions.

The nature of the composition and the pharmaceutical carrier or diluent will, of course, depend upon the intended route of administration, i.e. parenterally, topically, orally or by inhalation.

In general, particularly for the prophylactic treatment of asthma, the compositions will be in a form suitable for administration by inhalation. Thus the compositions will comprise a suspension or solution of the active ingredient in water for administration by means of a conventional nebulizer. Alternatively the compositions will comprise a suspension or solution of the active ingredient in a conventional liquified propellant or compressed gas to be administered from a pressurized aerosol container. The compositions may also comprise the solid active ingredient diluted with a solid diluent for administration from a powder inhalation device. In the above compositions, the amount of carrier or diluent will vary but preferably will be the major proportion of a suspension or solution of the active ingredient. When the diluent is a solid it may be present in lesser, equal or greater amounts than the solid active ingredient.

For parenteral administration the pharmaceutical composition will be in the form of a sterile injectable liquid such as an ampul or an aqueous or nonaqueous liquid suspension.

For topical administration the pharmaceutical composition will be in the form of a cream, ointment, liniment, lotion, pastes, and drops suitable for administration to the eye, ear, or nose.

For oral administration the pharmaceutical composition will be in the form of a tablet, capsule, powder, pellet, atroche, lozenge, syrup, liquid, or emulsion.

Usually a compound of formula I is administered to a subject in a composition comprising a nontoxic amount sufficient to produce an inhibition of the symptoms of a disease in which leukotrienes are a factor. When employed in this manner, the dosage of the composition is selected from the range of from 1 $\mu$g to 1000 mg. of active ingredient for each administration. For convenience, equal doses will be administered 1 to 5 times daily with the daily dosage regimen being selected from about 1 $\mu$g to about 5000 mg.

The pharmaceutical preparations thus described are made following the conventional techniques of the pharmaceutical chemist as appropriate to the desired end product.

Included within the scope of this disclosure is the method of treating a disease, pulmonary or nonpulmonary, in which leukotrienes are a factor which comprises administering to a subject a therapeutically effective amount of a prodrug compound of formula (I), preferably in the form of a pharmaceutical composition. For example, inhibiting the symptoms of an allergic response resulting from a mediator release by administration of an effective amount of a compound of fommula I is included within the scope of this disclosure. The administration may be carried out in dosage units at suitable intervals or in single doses as needed. Usually this method will be practiced when relief of symptoms is specifically required. However, the method is also usefully carried out as continuous or prophylactic treatment. It is within the skill of the art to determine by routine experimentation the effective dosage to be administered from the dose range set forth above, taking into consideration such factors as the degree of severity of the condition or disease being treated, and so forth.

Compounds of this invention, alone and in combination with a histamine $H_1$-receptor antagonist, act as prodrugs to generate compounds which inhibit antigen-induced contraction of isolated, sensitized guinea pig trachea (a model of respiratory anaphylaxis). Exemplary of histamine $H_1$-receptor antagonists are mepyramine, chlorpheniramine, and 2-[4-(5-bromo-3-methylpyrid-2-yl)butylamino]-5-[(6-methyl-pyrid-3-yl)methyl]-4-pyrimidone and other known $H_1$-receptor antagonists.

Pharmaceutical compositions, as described hereinabove, of the present invention also comprise a pharmaceutical carrier or diluent and a combination of a compound of the formula (I) or a pharmaceutically acceptable salt thereof, and an histamine $H_1$-receptor antagonist in amounts sufficient to inhibit antigen-induced respiratory anaphylaxis. The above-defined dosage of a compound of formula I is conveniently employed for this purpose and the known effective dosage for the histamine $H_1$-receptor antagonist. The methods of administration described above for the single active ingredient can similarly be employed for the combination with a histamine $H_1$-receptor antagonist. The following examples illustrate the preparation of the compounds of this invention and their incorporation into pharmaceutical compositions and as such are not to be considered as limiting the invention set forth in the claims appended hereto.

EXAMPLE 1

Preparation of Methyl 2-(carbomethoxymethylthio)-2-(2-dodecylphenyl)acetate

(a) 2-(2-Dodecylphenyl)-4,4-dimethyloxazoline

To freshly prepared dodecylmagnesium bromide (from 30.13 mmoles of dodecyl bromide and 26.20 mmoles of magnesium) in distilled tetrahydrofuran (50 ml) was added 2-(2-methoxyphenyl)-4,4-dimethyloxazoline [A.I. Meyers et al., *J. Org. Chem.*, 43, 1372 (1978)](17.88 mmoles) in tetrahydrofuran (30 ml). The resultant yellow solution was stirred under argon at ambient temperature for 20 hours. The solution was cooled in an ice water bath and quenched with aqueous ammonium chloride (100 ml). The reaction product was extracted into diethyl ether (100 ml) and the organic phase was washed with saturated sodium chloride solution (50 ml) and then dried over anhydrous magnesium sulfate. Evaporation of the organic phase afforded a colorless oil which was purified by flash chromatography over silica gel with 5 percent ethyl acetate in hexane as eluant to afford the desired product as a pale yellow oil.

Analysis for $C_{23}H_{37}NO$: Calculated: C, 80.41; H, 10.85; N, 4.08. Found: C, 80.22; H, 10.56; N, 3.87.

(b) 2-(2-Dodecylphenyl)-3,4,4-trimethyloxazolinium iodide

A solution of the compound of Example 1(a) (17.2 mmoles) in methyl iodide (20 ml) was refluxed under argon for 18 hours. The volatiles were removed under vacuum and the solid residue triturated with ethyl acetate (25 ml) to afford the desired product as white crystals (mp 78-84° C.).

(c) 2-Dodecylbenzaldehyde

To an ice cold solution of the compound of Example 1(b) (10.0 mmoles) in methanol (50 ml) over a period of 15 minutes was added in small portions sodium borohydride (10.0 mmoles). The reaction mixture was allowed to stir for 30 minutes and was then quenched with 5 percent sodium hydroxide (50 ml). The reaction mixture was extracted with diethyl ether (2×50 ml) and the extract was washed with brine (50 ml) and dried over anhydrous magnesium sulfate. Evaporation of the extract afforded an oil which was dissolved in acetone (50 ml) and 3N hydrochloric acid (10 ml) was added. The mixture was flushed with argon and stirred for 16 hours at ambient temperature. The volatiles were removed under vacuum and the residue partitioned between diethyl ether (50 ml) and water (50 ml). The aqueous phase was extracted with more diethyl ether (50 ml). The combined organic phase was washed with brine (50 ml) and dried over anhydrous magnesium sulfate. Evaporation of the organic phase yielded an oil which was purified by flash chromatography over silica gel with 2 percent ethyl acetate in hexane as eluant to afford the desired product as a colorless oil.

Analysis for $C_{19}H_{30}O$: Calculated: C, 83.15; H, 11.02. Found C, 82.59; H, 10.65.

Alternatively, 2-(1-dodecyn-1-yl)benzaldehyde is hydrogenated in the presence of 10% palladium-on-charcoal (see Example 7b) to give 2-dodecylbenzaldehyde.

(d) Methyl 2-(2-dodecylphenyl)-2-hydroxy acetate

The compound of Example 1(c) (17.2 mmoles) was dissolved in methylene chloride (20 ml) and stirred at 0° C. under argon. Zinc iodide (1.87 mmoles) was added, followed by the dropwise addition of trimethylsilyl cyanide (2.45 ml, 18.3 mmoles) dissolved in methylene chloride (30 ml). After 1 hour at 0° C. the ice bath was removed and the mixture stirred for 1 hour at room temperature. The solvent was stripped and methanol (100 ml) was added after the residue was cooled in an ice bath. Excess hydrogen chloride was bubbled into the solution while the mixture was stirred at ice bath temperature. The ice bath was then removed and the mixture stirred at room temperature for 18 hours. Water (20 ml) was added and the mixture stirred for 2 hours. The solvent was evaporated and the aqueous residue extracted with ethyl acetate. The combined organic phases were dried over anhydrous sodium sulfate, filtered and evaporated. The crude product was flash chromatographed on silica gel, eluted with 20% ethyl acetate/hexane, to give the product as a clear colorless liquid.

(e) Methyl 2-Chloro-2-(2-dodecylphenyl)acetate

The compound of Example 1(d) (12 mmoles) was stirred under argon in an ice bath and thionyl chloride (20 ml) was added in a single portion. The ice bath was removed and the mixture was stirred under argon for 18 hours. The solvent was stripped and the residue flash chromatographed on 200 grams of silica gel eluted with 20% methylene chloride/carbon tetrachloride to give the product as a clear colorless liquid.

(f) Methyl 2-(Carbomethoxymethylthio)-2-(2-dodecylphenyl)acetate

The compound of Example 1(e) (1.42 mmoles) was dissolved in methylene chloride (5 ml) and the mixture stirred at 0° C. under argon. Methyl thioglycolate (4.26 mmoles) was added, followed by triethylamine (1.56 mmoles). The ice bath was removed and the mixture stirred at room temperature for 2.5 hours. The solvent was evaporated and the residue flash chromatographed on 50 grams of silica gel eluted with 5-10% ethyl acetate/hexane to give the product as a clear colorless liquid. $^1H$ NMR (90 MHZ, $CCl_4$)δ 0.9 (t,3H), 1.1-1.6 (m,20H), 2.9-3.5 (m,2H), 3.65 (s,6H), 5.1 (s,1H), 7.1-7.2 (m,3H), 7.3-7.5 (m,1H).

Similarly, the following compounds are prepared according to the general methods of Example 1 from the 2-(2-methoxyphenyl)-4,4-dimethyloxazoline and the appropriate alkyl halide:

Methyl 2-(Carbomethoxymethylthio)-2-(2decylphenyl)acetate;

Methyl 2-(Carbomethoxymethylthio)-2-(2octylphenyl)acetate.

EXAMPLE 2

Preparation of Methyl 2-(2-carbomethoxyethylthio)-2(2-dodecylphenyl)acetate

The compound of Example 1(e) (3.04 mmoles) was dissolved in methylene chloride (10 ml) and stirred under argon at 0° C. Methyl 3-mercaptopropionate (3.3 mmoles) and triethylamine (3.3 mmoles) in methylene chloride (5 ml) was added dropwise over 5 minutes.

The ice-bath was removed and the mixture stirred under argon at room temperature for 2.5 days. Flash chromatography on 100 grams of silica gel eluted with 10% ethyl acetate/hexane gave the product as a clear colorless liquid. $^1$H NMR (90 MHZ, CCl$_4$) $\delta$0.9 (t,3H). 1.1–1.6 (m,20H), 2.3–2–8 (m,6H), 3.6 (s,3H), 3.7 (s,3H), 4.7 (s,1H), 7–7.1(m,3H), 7.3–7.5(m,1H).

EXAMPLE 3

Preparation of Methyl
2-(2-dodecylphenyl)-2(1,4-dimethyl-5-carbethoxy-2-imidazolylthio)acetate The compound of Example 1(e) (1 mmole), triethylamine (1.5 mmoles) and 1,4-dimethyl-2-mercapto-5-carbethoxyimidazole (1.33 mmoles) were dissolved in methylene chloride (25 ml) and stirred for 18 hours under argon. The solvent was stripped and the residue flash chromatographed on 50 grams of silica gel eluted with 15% ethyl acetate/hexane to give the product. $^1$H NMR (90 MHZ, CCL$_4$) $\delta$0.9 (t,3H), 1.1-1.8 (m,23H), 2.4 (s,3H), 2.8 (t,2H), 3.7 (s,3H), 3.8 (s,3H), 4.25 (q,2H), 5.8 (s,1H), 7.1–7.3 (m,3H), 7.3–7.5 (m,1H).

The following compounds are prepared by utilizing the general procedures for Example 3 from the appropriate starting materials:
Methyl 2-(2-Dodecylphenyl)-2-(1-methyl-2-imidazolylthio) acetate;
Methyl 2-(2-Dodecylphenyl)-2-(1-ethyl-5-carboxamido-2-imidazolylthio) acetate;
Methyl 2-(2-Dodecylphenyl)-2-(1-ethyl-2-imidazolylthio) acetate;
Methyl 2-(2-Dodecylphenyl)-2-(1-allyl-2-imidazolylthio) acetate;
Methyl 2-(2-Dodecylphenyl)-2-(1,4,5-trimethyl-2-imidazolylthio) acetate.

EXAMPLE 4

Preparation of
3-Aza-4-oxo-7-thia-8-(2-dodecyphenyl)nonanedioic acid dimethyl ester The compound of Example 1(e) (1.5 mmoles), methyl 3-aza-4-oxo-6-mercaptohexanoate (2.0 mmoles), and triethylamine (2.0 mmoles) were dissolved in methylene chloride (25 ml) and stirred under argon at room temperature for 5 days. The solvents were stripped and the residue flash chromatographed on 50 grams of silica el eluted with 50% ethyl acetate/hexane to give the product. $^1$H NMR (90 MHZ, CCL$_4$) $\delta$0.9 (t,3H), 1.1–1.7(m,20H), 2.2–2.9(m,6H), 3.7(s,6H), 3.9(d,2H), 4.8 (s,1H), 6.1–6.5(br d1H), 7–7.2(m,3H), 7.3–7.5(m,1H).

EXAMPLE 5

Preparation of Methyl
2-(2-dodecylphenyl)-2-(1-methyl-4-propyl-5-carbethoxy-2-imidazolylthio)acetate The compound of Example 1(e) (1 mmole), 1-methyl-2-mercapto-4-propyl-5-carbethoxyimidazole (1.33 mmoles), and triethylamine (1.5 mmoles) were dissolved in methylene chloride (25 ml) and stirred under argon at room temperature for 18 hours. The reaction mixture was warmed to reflux for 8 hours and then stirred at room temperature for 18 hours. The solvents were stripped and the residue flash chromatographed on 50 grams of silica gel eluted with 10% ethyl acetate/hexane to give the product as a clear colorless oil. $^1$H NMR (90 MHZ, CCl$_4$) $\delta$0.7–1 (m.6H). 1.1–1.9(m,27H). 2.8(t.2H), 2.6(s.3H). 3.7(s.3H). 4.25(q.2H). 5.8(s.1H). 7.1–7.2(m.3H). 7.3–7.5(m,1H).

EXAMPLE 6

Preparation of Methyl
2-(3-carboxypropylthio)-2-(2-dodecylphenyl)acetate

The compound of Example 1(e) (1 mmole), 4-mercaptobutyric acid (1.33 mmoles), and triethylamine (3 mmoles) were dissolved in methylene chloride (25 ml) and stirred at room temperature under argon for 5 days. The solvents were pumped off and the residue flash chromatographed on 50 grams of silica gel eluted with 6:3:1 methylene chloride:ethanol:ammonium hydroxide. The eluant was concentrated, acidified with hydrochloric acid, extracted with ethyl acetate, dried over anhydrous sodium sultate, filtered and evaporated to give the product. $^1$H NMR (90 MHZ, CDCl3) $\delta$O.9(t,3H), 1.1–2.8(m,28H), 3.6(s,3H), 4.8(s,1H), 7–7.2(m,3H), 7.4–7.5 (m,1H).

EXAMPLE 7

Preparation of Methyl
2-(2-carbomethoxyethylthio)-2-[2-(8-phenyloctyl)phenyl]acetate (a) 2-(8-Phenyloctyl)benzaldehyde A solution of 6-phenylhexanoic acid (19.8 mmoles in sieve dried tetrahydrofuran (5 ml) was reduced with diborane in tetrahydrofuran (30 ml, 29.1 mmoles) at 0° C. for 4 hours to give 6-phenylhexanol. To an ice cold solution of the hexanol (ca. 19.8 mmoles) and carbon tetrabromide (21.98 mmoles) in methylene chloride (50 ml) was added triphenylphosphine (22.30 mmoles) in methylene chloride (50 ml) and the resultinq solution was stirred for 2.5 hours. The volatiles were evaporated and the residue was taken up in ether (100 ml), cooled in ice, and filtered. The filtrate was evaporated and distilled to afford 6-phenylhexyl bromide as an oil.

Following the procedures of Example 1(a), (b) and (c), to 8-phenyloctylmagnesium bromide (from 24.25 mmoles of 8-phenyloctyl bromide and 21.27 mmoles of magnesium) in distilled tetrahydrofuran (40 ml) was added 2-(2-methoxyphenyl)-4,4-dimethyloxazoline (17.10 mmoles) in tetrahydrofuran (20 ml). After stirring for 24 hours, the reaction mixture was similarly worked up to yield 2-[2-(8-phenyloctyl)phenyl]-4,4-dimethyloxazoline as an oil. A solution of the oxazoline (11.58 mmoles) in methyl iodide (20 ml) was refluxed under argon for 18 hours. Removal of the volatiles afforded the corresponding 3,4,4-trimethyloxazolinium iodide as a white solid (mp 76.5–78° C.). To an ice cold solution of the iodide (9.46 mmoles) in methanol (35 ml) was added in portions sodium borohydride (9.20 mmoles). Treatment of the reaction mixture as in Example 1(c) results in the isolation of the desired product as an oil.

Analysis for C$_{21}$H$_{26}$O: Calculated: C, 85.67; H, 8.90. Found: C, 85.12, 85.22; H, 8.94, 8.96.

(b) Alternative preparation of
2-(8-phenyloctyl)benzaldehyde

A solution of 5-hexynyl alcohol (102 mmoles) in pyridine (150 ml), under argon was cooled to 0° C. and p-toluenesulfonyl chloride (204 mmoles) was added. The reaction mixture was kept at about 4° C. for 18 hours, poured into ice-water and then taken up in ether. The ether extract was washed with cold 10% hydrochloric acid, water and brine. The organic layer was dried and concentrated in vacuo to give 5-hexynyl p-toluenesulfonate. A solution of phenylacetylene (97 mmoles) in tetrahydrofuran (200 ml) containing a trace of triphenylmethane was cooled to 0° C. and then n-butyl lithium (37.3 ml of 2.6 moles in hexane) was added dropwise. The resulting solution was stirred at 0° C. for 10 minutes and hexamethylphosphoramide (21 ml) was added dropwise. After stirring for 10 minutes a solution of 5-hexynyl p-toluenesulfonate (97.1 mmoles) in tetrahydrofuran (200 ml) was added. The reaction mixture was stirred at room temperature for 18 hours, diluted with ether and the organic layer was washed with water and brine. The dried organic solution was concentrated and the product was purified by flash chromatography to give 1-phenylocta-1,7-diyne. A mixture of this compound (43 mmoles), 2-bromobenzaldehyde (35.8 mmoles), cuprous iodide (0.5 mmoles) and bis(triphenylphosphine) palladium (II) chloride (0.7 mmoles) in triethylamine (100 ml) was heated in an oil bath (95° C.) for one hour. The reaction mixture was cooled to 0° C. filtered and the filtrate was concentrated. The residue was dissolved in ether, washed with 10% hydrochloric acid, water and brine. The organic layer was dried and concentrated to give a product which was purified by flash chromatography to yield 2-(8-phenyl1,7-octadiynyl)benzaldehyde. A solution of this compound (24.1 mmoles) in ethyl acetate (100 ml) and 10% palladium on charcoal (1 g) was hydrogenated (40 psi of hydrogen) at room temperature for 15 minutes. The catalyst was filtered off and the filtrate concentrated to qive the 2-(8-phenyloctyl)benzaldehyde.

(c) Methyl 2-[2-(8-phenyloctyl)phenyl]-2-hydroxy acetate

The compound of Example 7(a) or 7(b) (10 mmoles) was dissolved in methylene chloride (10 ml) and stirred at ° C. under argon. Zinc iodide (1.1 mmoles) was added followed by the dropwise addition of trimethylsilyl cyanide (1.47 ml, 11 mmoles) dissolved in methylene chloride (20 ml). After 1 hour at 0° C. the ice bath was removed and the mixture stirred for 1 hour at room temperature. The solvent was stripped and methanol (60 ml) was added at ice bath temperature. Excess hydrogen chloride was bubbled into the solution while stirring. The ice bath was removed and the mixture stirred at room temperature for 18 hours. Water (12 ml) was added and the mixture stirred for 2 hours. The solvent was evaporated and the residue extracted with ethyl acetate, dried over anhydrous sodium sulfate, filtered and evaporated. The crude product was flash chromatographed on 200 grams of silica gel eluted with 20% ethyl acetate/hexane to give the product as a clear colorless liquid.

(d) Methyl 2-chloro-2-[2-(8-phenyloctyl)phenyl]acetate

The compound of Example 7(c) (6.8 mmoles) was stirred under argon in an ice bath and thionyl chloride (15 ml) was added in a single portion. The ice bath was removed and the reaction mixture was stirred for 18 hours. The solvent was stripped and the residue flash chromatographed on 100 grams of silica gel eluted with 20% methylene chloride/carbon tetrachloride to give the product as a clear colorless liquid.

(e) Methyl 2-(2-carbomethoxyethylthio)-2-[2-(8-phenyloctyl)phenyl]acetate

The compound of Example 7(d) (5.4 mmoles), methyl 3-mercaptopropionate (5.9 mmoles), and triethylamine (5.9 mmoles) were dissolved in methylene chloride (30 ml) and stirred under argon at room temperature for 5 days. The solvents were stripped and the residue was flash chromatographed on 100 grams of silica gel eluted with 10% ethyl acetate/hexane to qive the product as a clear colorless liquid. $^1$H NMR (90 MHZ, CCl$_4$)δ 1.2–1.9(m,12H), 2.4–2.9(m,8H), 3.6(s,3H), 3.7(s,3H), 4.8(2,1H), 7–7.3(m,8H), 7.4–7.6(m,1H).

EXAMPLE 8

Preparation of Methyl 2-(2-carboxamidoethylthio)-2-(2-dodecylphenyl)acetate (a) 3-Mercaptopropionamide To a suspension of 3,3'-dithiodipropionic acid (0.04 mole) in chloroform (250 ml) was added thionyl chloride (21 ml) and4 drops of dimethylformamide. The mixture was heated under reflux for one hour and allowed to stand at room temperature for 18 hours. The reaction mixture was concentrated in vacuo and azeotroped with toluene. The residual oil (acid chloride) was dissolved in a small amount of ether and added to cold concentrated ammonium hydroxide (25 ml) dropwise, with stirring. The stirring was continued for 15 minutes. The mixture was filtered and washed with a large volume of cold water. A white solid was obtained which was oven-dried to give 3'3-dithiodipropionamide, mp 178–180° C. To a solution of this amide (28.8 mmoles) in acetone (200 ml) was added tri-n-butylphosphine (63.5 mmoles) followed by water (200 ml). This mixture was stirred at room temperature for 18 hours. The reaction mixture was concentrated in vacuo, azeotroped with excess toluene and the residual oil was treated with ether. The separated solid was filtered, redissolved in methylene chloride, dried over magnesium sulfate, filtered and concentrated to qive the solid product, mp 100–101° C.

(b) Methyl 2-(2-Carboxamidoethylthio)-2-(2-dodecylphenyl)acetate

To a solution of the compound of Example 1(e) (1 mmole) and the compound of Example 8(a) (1.33 mmoles) in methylene chloride (10 ml) was added triethylamine (1.5 mmoles) and the mixture was stirred at room temperature for 48 hours. The reaction mixture was washed with water, 5% potassium carbonate solution and water, dried and concentrated. The residual oil solidified upon cooling and trituration with ether to give the product, mp 119–120° C.

EXAMPLE 9

Preparation of t-Butyl 3-(2-carboxyethylthio)-3-(2-dodecylphenyl)propionate (a) t-Butyl 3-(2-dodecylphenyl)propenoate The compound of Example 1(c) (32 mmoles) was dissolved in toluene (50 ml) and cooled to 0° C. in an ice-water bath while stirring under argon. t-Butyl (triphenylphosphoranylidene)acetate (32 mmoles) was added in one portion. The mixture was heated at 110° C. for 24 hours. The toluene was evaporated and the resulting residue was flash chromatographed using a 6% ethyl acetate in hexane system to give the product.

(b) t-Butyl 3-(2-carboxyethylthio)-3-(2-dodecylphenyl)propionate

Sodium (155.5 mmoles) was added slowly to methanol (200 ml) under an atmosphere of argon. The mixture was cooled to 0° C. in an ice bath and 3-mercaptopropionic acid (78 mmoles) was added dropwise. This mixture was stirred for 30 minutes and the compound of Example 9 (a) (7.8 mmoles) was added dropwise. The reaction mixture was stirred for 24 hours. The solvent was evaporated. The residue was taken up in ice water and acidifed with 10% phosphoric acid to a pH of 6.5. The product was extracted into ethyl acetate. The combined organic extracts were dried over magnesium sulfate, filtered and evaporated. The resulting residue was flash chromatographed with 1.0% methanol and 1.0% formic acid in methylene chloride. This provided the product as an oil.

$^1$H NMR δ: 7.4(m), 7.1(d), 4.6(t), 2.7(m), 1.4(s).

EXAMPLE 10

Preparation of di-(t-Butyl)-3-aza-4-oxo-7-thia-8-(2-dodecylphenyl)decanedioate

A mixture of the compound of Example 9(b) (1.3 mmoles) and methylene chloride (4 ml) was cooled to 0° C. in an ice-methanol bath under argon. To this mixture was added glycine t-butyl ester (1.3 mmoles) in methylene chloride (4 ml) and 1,3-dicyclohexylcarbodiimide. The ice bath was removed and the reaction was stirred for 24 hours. The reaction mixture was filtered, then concentrated. The resulting residue was flash chromatographed on silica eluted with 20% ethyl acetate in hexane to afforded the product. $^1$H NMR δ: 7.3(m), 7.1(d), 6.2(m), 4.6(t), 3.8(d), 2.7(m), 1.5(s), 1.3(d).

EXAMPLE 11

Preparation of Methyl 2-methyl-3-(2-carboxyethylthio)-3(2-dodecylphenyl)-propanoate (a) Methyl 2-methyl-3-hydroxy-3-(2-dodecylphenyl)propanoate To a suspension of zinc dust (15 mmoles) and copper (I) bromide (5 mmoles) in distilled tetrahydrofuran (10 ml) at 25° C. was added diethylaluminum chloride (10 mmoles). The mixture was stirred for 5 minutes, then cooled to 0° C. in an ice-methanol bath. A solution of the compound of Example 1(c) (10 mmoles) and methyl d,1-2-bromopropionate (10 mmoles) in tetrahydrofuran (10 ml) was added dropwise to the cold suspension. The resulting mixture was stirred for 3 hours at 25° C. The reaction mixture was filtered and the filtrate was washed with water, dried over magnesium sulfate, and evaporated to give the product.

(b) Methyl 2-methyl-3-(2-carboxyethylthio)-3-(2-dodecylphenyl)-propanoate

To a solution of trifluoroacetic acid (15 ml) and 3-mercaptopropionic acid (2.4 ml) at 0° C. was added the compound of Example 11(a). The reaction mixture was stirred for 3 hours and evaporated. The resulting residue was flash chromatographed on silica, eluted with 20% ethyl acetate in hexane, to give a mixture of erythro and threo isomers of the product. $^1$H NMR (CDCl$_3$)δ: 0.9 (t, J=6.5Hz,3H), 1.35(m,23H), 2.5(m,6H), 3.0(t, J=6.5,1H), 3.5(s,3H), 4.5(d,J=6.5,1H), 7.2(m,3H), 7.5(m,1H), 10(bs,1H). $^1$H NMR (CDCl$_3$)δ: 0.9(t,J=6Hz,3H), 1.3(m,23H), 2.5(m,6H), 3.0(dd, J=6Hz, 11Hg, 1H), 3.75(s,3H), 4.3(d, J=11Hz,1H), 7.2(m,4H), 9.2(bs,1H).

EXAMPLE 12

Preparation of t-Butyl 3-(2-carboxyethylthio)-3-[2-(8-phenyloctyl)-5-trifluoromethylphenyl]propanoate (a) 2-(8-Phenyloctyl)-5-trifluoromethyl benzaldehyde To a solution of 2-bromo-5-trifluoromethyl benzonitrile (20.16 mmoles) in methylene chloride (50 ml), under argon at room temperature, was added diisobutylaluminum hydride (25 mmoles, 25 ml hexane) dropwise and the resulting solution was stirred for 30 minutes. The reaction mixture was diluted with ether (50 ml), cooled in ice and quenched by the careful addition of hydrochloric acid (50 ml, 3N). The ice bath was removed and the mixture was stirred vigorously for 15 minutes. The organic layer was washed with brine (50 ml), treated with magnesium sulfate-charcoal and evaporated. The resulting oil was purified by distillation to give 2-bromo-5-trifluoromethyl benzaldehyde, bp 50–55° C. at 0.05 mm Hq. A mixture of this compound (16.24 mmoles), 1-phenylocta-1,7-diyne (19.54 mmoles, prepared as in Example 7b), cuprous iodide (0.19 mmole) and bis(triphenylphosphine) palladium (II) chloride (0.34 mmole) in triethylamine (50 ml) was refluxed under argon for 30 minutes. The reaction mixture was cooled and filtered. The filtrate was evaporated, taken up in ether (100 ml), washed with hydrochloric acid (50 ml, 3N) and sodium chloride, and treated with magnesium sulfate-charcoal. Filtration and evaporation left an oil which was purified by flash chromatography (5% ether/hexane) to yield 2-(8-phenyloctadiyn-1,7-yl)-5-trifluoromethyl benzaldehyde as an oil. A solution of this compound (13.26 mmoles) in ethyl acetate (100 ml) was treated with charcoal for 30 minutes and then filtered. The solution was then shaken under 50 psi of hydrogen with 10% palladium on charcoal (502 mg) for about 90 minutes. Thin layer chromatography of the reaction mixture indicated about 50% reduction of the aldehyde to the alcohol. To re-oxidize the alcohol, the palladium catalyst was filtered off and manganese dioxide (20 q) was added. This mixture was then stirred at room temperature under argon for 18 hours. Filtration and evaporation gave an oil which was purified by flash chromatography (2% ether/hexane) to afford the product as an oil.

(b) t-Butyl 3-[2-(8-phenyloctyl)-5-trifluoro methylphenyl]-3-hydroxypropanoate

The compound of Example 12(a) (5.1 mmoles) in tetrahydrofuran (7 ml) and trimethyl borate (7 ml) were added dropwise with stirring to zinc metal (8.8 mmoles) at 25° C. After 5 minutes, t-butyl bromoacetate (6.79 mmoles) was added all at once and the mixture was stirred for 24 hours. An additional 2 ml. of t-butyl bromoacetate was added and the mixture stirred at room temperature for 36 hours. The reaction mixture was diluted with ether, cooled to 0° C, and ice-cold ammonium hydroxide/water/glycerine was added dropwise with stirring. The organic layer was washed with water and brine, dried over magnesium sulfate and concentrated. The residue was flash chromatographed in silica, eluted with 5% ethyl acetate/hexane, to give the product as a clear colorless oil.

(c) t-Butyl 3-[2-(8-phenyloctyl)-5-trifluoromethylphenyl]-3-methanesulfonyloxypropanoate The compound of Example 12(b) (2.0 mmoles) was dissolved in methylene chloride (10 ml) under argon and the solution cooled to −10° C. Triethylamine (6.6 mmoles) was added and then methanesulfonyl chloride (2.2 mmoles) in methylene chloride (3 ml) was added dropwise. The mixture was stirred in the cold for 30 minutes and poured into ice/water/methylene chloride. The separated organic layer was washed with cold ammonium chloride solution, water and brine, and then dried and concentrated to give the product as an oil.

(d) t-Butyl 3-[2-(8-phenyloctyl)-5-trifluoromethylphenyl]propenoate

The compound of Example 12(c) (1.97 mmoles) was dissolved in methylene chloride (10 ml) under argon and the solution cooled to 0° C. Triethylamine (6.3 mmoles) in methylene chloride (5 ml) was added dropwise and the mixture allowed to warm to room temperature for 18 hours and poured into ice/water/methylene chloride. The separated organic layer was washed with cold ammonium chloride solution, water and brine, and then dried and concentrated to give the product as an oil.

Alternatively, the compound of Example 12(a) is reacted with t-butyl (triphenylphosphoranylidene)acetate to give the product of Example 12(d).

(e) t-Butyl 3-(2-carboxyethylthio)-[2-(8-phenyloctyl)-5-trifluoromethylphenyl]propanoate Following the procedure of Example 9(b) the compound of Example 12(d) (1.86 mmoles) was converted to the named product. $^1$H NMR (CDCl$_3$) 90 MHz, δ: 1.2–1.85 (m,21H), 2.45–2.9(m,10H), 4.5–4.75 (t,1H), 7.1–7.7(m,8H), 9.75–10.15 (broad s,1H).

EXAMPLE 13

Preparation of Methyl 4-thia-5-(2-dodecylphenyl)-5-(tetrazol-5-yl)pentanoate

(a) 2-Dodecylbenzoic acid

A solution containing lithium diisopropylamide (0.1 mole) was prepared by treating a solution of dissopropylamine (14.1 ml, 0.1 mole) in tetrahydrofuran (200 ml) at 0° C. with n-butyl lithium (41.2 ml of a 2.43 M solution, 0.1 mole), and stirring for 5 minutes. To this was added a solution of o-toluic acid (6.8 g, 0.05 mole) in tetrahydrofuran (50 ml). The ice bath was removed and the intense red solution was stirred for 30 minutes. This solution was slowly pipetted into a solution of undecylbromide (11.8 g, 0.05 mole) in tetrahydrofuran (50 ml) at −20° C. After the addition, the cooling bath was removed and the solution stirred for 30 minutes. A small amount of water was added and most of the tetrahydrofuran was removed under reduced pressure. The residue was poured into water, acidified with 3N hydrochloric acid and extracted with ether. The ether was dried, evaporated and the residue was recrystallized from acetonitrile, then from hexane, to give the product.

(b) 2-Dodecylbenzyl alcohol

A solution of the compound of Example 13(a) (19.0 g, 66 mmoles) in ether (200 ml) was slowly added to a stirred slurry of lithium aluminum hydride (2.5 g, 66 mmoles), in ether (500 ml), at 0° C. The ice bath was removed and stirring continued 2 hours. Water (2.5 ml) was cautiously added, followed by 10% sodium hydroxide solution (3.74 ml) and water (6.25 ml). The solids were filtered, the filtrate was evaporated and the crude residue was recrystallized from acetonitrile to give the product.

(c) 2-Dodecylbenzyl nitrile

A solution of the compound of Example 13(b) (11.7 q, 42 mmoles) in a mixture of methylene chloride (300 ml) and pyridine (5.1 ml, 63 mmoles) at 0° C. was treated slowly with thionyl chloride (7.5 g, 63 mmoles). The ice bath was removed and stirring continued for 4 hours. The solvents were evaporated and the residue taken up in ether. The ether was washed with water, dried and evaporated to give crude 2-dodecylbenzyl chloride.

This crude chloride was dissolved in dimethylformamide (20 ml) and added to a cold (0° C.) suspension of potassium cyanide (4.13 g, 63 mmoles) in dimethylformamide (50 ml). The ice bath was removed and stirring was continued for 18 hours at 23° C. and 30 minutes at 95° C. The reaction mixture was poured onto ice and extracted with ether. The extract was washed with water, dried and evaporated. The residue was recrystallized from methanol to give the product.

(d) 5-(2-Dodecylbenzyl)tetrazole

A mixture of the compound of Example 13(c) (4.0 g, 14 mmoles), sodium azide (5.48 g, 84 mmoles) and ammonium chloride (4.5 g, 83 mmoles) in dimethylformamide (50 ml), under argon, was heated at 135° C. for 30 hours. The mixture was cooled, poured into water (100 ml), acidified with concentrated hydrochloric acid and extracted thoroughly with ether. The extracts were washed several times with water, dried and evaporated. The crude product was recrystallized from acetonitrile to give the product.

(e) Methyl 4-thia-5-(2-dodecylphenyl)-5-tetrazol-5-yl)pentanoate

A solution of diisopropylamine (0.85 ml, 6.1 mmoles) in tetrahydrofuran (10 ml) at 0° C. was treated with n-butyl lithium (6.1 mmoles). After 5 minutes a solution of the compound of Example 13(d) (1.0 g, 3.05 mmoles) in tetrahydrofuran (5 ml) was added. The deep yellow solution was stirred for 30 minutes and then cooled to −78° C. A solution of 2-carbomethoxyethyl-p-toluenethiosulfonate (0.84 g, 3.05 mmoles) in tetrahydrofuran (5 ml) was added. The solution was warmed to 23° C, stirred for 30 minutes and poured into water (100 ml). The mixture was acidified with 3N hydrochloric acid and extracted with ethyl acetate. The extract was washed with water and 1N hydrochloric acid, dried and evaporated. The crude product was chromatographed over silica gel, eluting with hexane/ethyl acetate, 7:3, to give the product.

The 2-carbomethoxyethyl-p-toluenethiosulfonate used as above was obtained by reaction of a solution of di-2-carbomethoxyethyl disulfide (6.66 g, 28 mmoles) in acetone (200 ml) with a solution of silver nitrate (4.76 g, 28 mmoles) in water (20 ml), followed by a solution of sodium p-tolenesulfinate (6.0 g, 28 mmoles) in warm water (60 ml). After stirring for 1 hour, the reaction mixture was filtered. The filtrate was concentrated and extracted with ethyl acetate. The extract was washed with water, dried and evaporated to give the desired thiosulfonate.

$^1$H NMR (CDCl$_3$)δ: 7.03–7.37(m,4H), 5.77(s,1H), 3.77(s,3H), 2.47–3.00 (m,6H), 1.07–1.83(m,20H), 0.87(t,3H).

EXAMPLE 14

Preparation of Methyl 4-thia-5-(2-dodecylphenyl)-5-carboxamidopentanoate (a) 2-(2-Dodecylphenyl)acetic acid A solution of the compound of Example 13(c) (5.4 g, 19 mmoles) and sodium hydroxide (4.0 g, 0.1 mole) in water (20 ml) and ethanol (60 ml) was refluxed for 8 hours. Water (100 ml) was added and the mixture was filtered. The filtrate was acidified with 3N hydrochloric acid and the resulting solid was extracted into ethyl acetate. The extract was dried and evaporated to give the product.

(b) 2-(2-Carbomethoxyethylthio)-2-(2-dodecylphenyl)acetic acid

A solution of diisopropylamine (4.6 ml, 33 mmoles) in tetrahydrofuran (40 ml) at −20° C. was treated with n-butyl lithium (36 mmoles). After 5 minutes the temperature was raised to 0° C. and a solution of the compound of Example 14(a) 5.0 q, 16.4 mmoles) in a mixture of tetrahydrofuran (10 ml) and hexamethylphosphoramide (5 ml) was added. After stirring for 1 hour, this solution was slowly added to a solution of 2-carbomethoxyethyl-ptoluenethiosulfonate (5.98 g, 16.4 mmoles) in tetrahydrofuran (30 ml) at −78° C. After 30 minutes, water (200 ml) was added to the cold reaction mixture. It was warmed to 23° C. acidified with 3N hydrochloric acid and extracted with ethyl acetate. The extracts were washed with water, 1N hydrochloric acid, dried and evaporated. The crude residue was chromatographed over silica gel, eluted with a mixture of hexane:ethyl acetate:acetic acid, 80:19.5:0.5, to qive the product as an oil.

(c) 2-(2-Carbomethoxyethylthio)-2-(2-dodecylphenyl)acetyl chloride

A solution of the compound of Example 14(b) (500 mg, 1.18 mmoles) in methylene chloride (15 ml) was stirred under argon at room temperature, and oxalyl chloride (0.115 ml, 1.3 mmoles) was added followed by pyridine (0.01 ml, 0.12 mmole). The reaction mixture was stirred at room temperature for 30 minutes and the solvent was removed to give the product.

(d) Methyl 4-thia-5-(2-dodecylphenyl)-5-carboxamidopentanoate

To the compound of Example 14(c) (330 mg, 0.75 mmole), stirred in an ice bath under argon, was added concentrated ammonium hydroxide (2 ml) and the mixture stirred for 15 minutes. The reaction mixture was diluted with water, extracted with ethyl acetate, dried over anhydrous sodium sulfate, filtered and evaporated to give the product. $^1$H NMR (90 MHZ, CCl$_4$)δ0.9 (t,3H), 1.1–1.8(m,20H), 2.5–3(m,6H), 3.6(s,3H), 4.65(s,1H), 6.6–7.7(m,6H).

EXAMPLE 15

Preparation of Methyl 2-(2-dodecylphenyl)-5-sulfo-3-thiapentanoate

The compound of Example 1(e) (0.75 g, 2.13 mmoles) was dissolved in methylene chloride (5 ml) under argon and triethylamine (0.41 ml, 2.98 mmoles) was added, followed by sodium thioethylsulfonate (0.49 g, 2.98 mmoles). Dimethylformamide (7 ml) was added and the mixture stirred at room temperature for 72 hours. The reaction mixture was poured into ice cold 3N hydrochloric acid/ethyl acetate. The separated organic layer was washed with water, until neutral pH, and sodium chloride solution, dried and concentrated to give the product. $^1$H NMR (CDCl$_3$) 90 mHz, δ: 0.75–1.0 (m,3H), 1.15–1.45(m,20H), 2.5–2.85(m,2H), 3.0–3.3(m,4H), 3.65(s,3H), 4.95(s,1H), 7.05–7.25(m,3H), 7.35–7.55(m,1H).

EXAMPLE 16

Preparation of 5-Carbomethoxy-5-(2-dodecylphenyl)-3-carboxy-4-thiapentanoic acid The compound of Example 1(e) (0.99 q, 2.8 mmoles) was dissolved in dimethylformamide (10 ml), and triethylamine (2.2 ml, 15 8 mmoles) was added followed by 2-thiobutanedioic acid (0.59 q, 3.94 mmoles). After about 10 minutes, additional triethylamine (1 ml) and dimethylformamide (10 ml) were added and stirring was continued at room temperature for 12 hours, under argon. The reaction mixture was poured into ice cold 10% hydrochloric acid/ethyl acetate and the layers separated. The organic layer was washed with water and saturated sodium chloride solution, and then dried over magnesium sulfate to give after evaporation the product as a mixture of 2 stereo isomers. $^1$H NMR (CDCl$_3$) 90MHz, δ: 0.8–1.0(m,3H), 1.2–1.5(m,20H), 2.6–3.05(m,5H), 3.75(s,3H), 5.3(s,1H), 7.1–7.3(m,4H), 9.8–10.0(broad s,2H).

EXAMPLE 17

Preparation of Methyl 2-(2-sulfonamidoethylthio)-2-(2-dodecylphenyl)acetate (a) Methyl 2-(2-chlorosulfonylethylthio-2-(2-dodecylphenyl)acetate The compound of Example 15(a) (1 g, 2.18 mmoles) was dissolved in dimethylformamide (5 ml), and thionyl chloride (0.19 ml, 2.62 mmoles) in dimethylformamide (1 ml) was added dropwise. The mixture was maintained at 0° C. for 1 hour and then cooled at −15° C. for 18 hours. The reaction mixture was warmed to 0° C., additional thionyl chloride (0.1 ml) was added and stirring was continued at 0° C. for 1 hour. The mixture was poured into ice water/ethyl acetate and the organic layer was washed with water and sodium chloride solution, then dried and concentrated. The residue was flash chromatographed on a silica column, eluted with 1–2% ethyl acetate/hexane/0.5% formic acid, to give the product as an oil.

(b) Methyl 2-(2-sulfonamidoethylthio-2-(2-dodecylphenyl)acetate

To the compound of Example 17(a) (0.29 g, 0.609 mmole), chilled in ice/methanol, was added ice cold ammonium hydroxide (3 ml). The mixture was stirred for 1 minute, diluted with ethyl acetate and then water was added. The organic layer was washed with water and sodium chloride solution, then dried over magnesium sulfate and concentrated to give an oil. The oil was flash chromatographed on a silica column, eluted with 25% ethyl acetate/hexane/0.5% formic acid, to qive the product as an oil. $^1$H NMR (CDCl$_3$) 90 MHz, δ: 0.75–1.0(m,3H), 1.2–1.5(m, 20H), 2.6–2.85 (t,2H), 2.9–3.15(m,2H), 3.2–3.45(m,2H), 3.75(s,3H), 4.95(s,1H), 5.0–5.1(broad s,2H), 7.15–7.25(m,3H), 7.4–7.6(m,1H).

EXAMPLE 18

Preparation of Methyl 4-thia-5-(2-dodecylphenyl)-6-(tetrazol-5-yl)hexanoate (a) Ethyl 2-(tetrazol-5-yl)-2((2-dodecylbenzoyl)acetate A solution of i-propylcyclohexylamine (4.6 ml, 28 mmoles) in tetrahydrofuran (25 ml) at −20° C. was treated with a 2.12 M solution of n-butyl lithium in hexane (13.2 ml, 28 mmoles). After stirring for 30 minutes, the solution was cooled to −78° C. and a solution of ethyl 2-(tetrazol-5-yl)acetate (2.17 g, 14 mmoles) in tetrahydrofuran (5 ml) and hexamethylphosphoramide (5 ml) was added. The temperature was raised to −20° C. and the solution stirred for 1 hour.

2-Dodecylbenzoyl chloride was prepared from 2-dodecylbenzoic acid (4.06 q, 14 mmoles) and excess thionyl chloride in methylene chloride at 23° C. for 1 hour. Following evaporation of the solvents, the acid chloride was used without purification. A solution of this acid chloride in tetrahydrofuran (15 ml) was added to the cold solution of dianion prepared above, followed by an additional amount of 2.12 M n-butyl lithium (6.6 ml). The solution was warmed to −20° C., stirred for 1 hour and poured into cold 1N hydrochloric acid. The mixture was extracted with diethyl ether. The extracts were washed with water, dried and evaporated. The crude product was recrystallized from acetonitrile (b) α-(Tetrazol-5-yl)-2-dodecylacetophenone A solution of the compound of Example 18(a) (3.5 g, 8.2 mmoles) in acetic acid (12 ml) and concentrated hydrochloric acid (12 ml) was refluxed for 4 hours. After cooling and dilution with water (50 ml), the solid was filtered and washed with water. The solid was dissolved in chloroform, washed with water, dried and evaporated to qive the product.

(c) α-(5-Tetrazolylmethyl)-2-dodecylbenzyl alcohol

A solution of the compound of Example 18(b) (2.24 g, 6.3 mmoles) in ethanol (20 ml) was treated with excess sodium borohydride and stirred at 23° C. for 4 hours. The reaction mixture was poured into water, acidified and extracted with a mixture of ether and ethyl acetate. The extracts were washed with water, dried and evaporated. The residue was chromatographed over silica gel. Elution with chloroform washed off impurities, then elution with a mixture of ethyl acetate in chloroform, 4:6, gave the product.

(d) Methyl 4-Thia-5-(2-dodecylphenyl)-6-(tetrazol-5-yl) hexanoate

A solution of the compound of Example 18(c) (0.3 g, 0.84 mmole) in trifluoroacetic acid (5 ml) and methyl mercaptopropionate (0.5 ml) was heated at 70° C. for 20 minutes, and then thoroughly evaporated. The residue was chromatographed over silica gel, eluting first with chloroform to remove impurities. Elution with a mixture of ethyl acetate and chloroform, 1:1, gave the product. $^1$H NMR (CDCl$_3$)δ: 7.00–7.43 (m,4H), 4.52(t,1H), 3.63(s,3H), 3 52(d,2H), 2.32–2.82(m,6H), 1.05–1.65(m,20H), 0.80(t,3H).

EXAMPLE 19

Preparation of Methyl 2-(2-cyanoethylthio)-2-(2-dodecylphenyl)acetate

To a solution of the compound of Example 1(e) (704 mg, 2 mmoles) and 3-mercaptopropionitrile (232 mg, 2.66 mmoles) in methylene chloride (5 ml) was added triethylamine (3 mmoles) and the mixture was stirred at room temperature for 48 hours. The reaction mixture was washed with water, 5% potassium carbonate solution, water, dried, filtered and concentrated to give the product as an oil.

EXAMPLE 20

Preparation of 2-Hydroxy-3-[(2-carboisopropoxyethyl) thio]-3-[2-(8-phenyloctylphenyl)]propanoic acid.

(a) Methyl 3-[2-(8-phenyloctyl)phenyl]-2,3-epoxypropionate

The compound of Example 7(a) (2.94 q, 10 mmoles) was dissolved in diethyl ether (25 ml) and the solution was stirred under argon at 0° C. Methyl chloroacetate (1.32 ml, 15 mmoles) was added, followed by the addition of sodium methoxide (810 mg, 15 mmoles). The mixture was stirred for 2.5 hours at ice bath temperature. A small quantity of water was added, the ether phase separated, dried over anhydrous sodium sulfate, filtered and evaporated. The residue was flash chromatographed on 80 grams of silica gel eluted with 5–30% ethyl acetate/hexane to give the product.

(b) Methyl 3-(2-carbomethoxyethylthio)-3-[2-(8-phenyloctyl)-phenyl]-2-hydroxypropanoate The compound of Example 20(a) (1.2 g, 3.28 mmoles) was dissolved in methanol (20 ml) containing 2% triethylamine and stirred under argon at room temperature. Methyl 3-mercaptopropionate (0.623 ml, 5.45 mmoles) and triethylamine (1.45 ml, 9.84 mmoles) were dissolved in methanol (15 ml) and added dropwise. The mixture was stirred for 18 hours. The solvent was stripped and the residue eluted with 20% ethyl acetate/hexane to give a mixture of the desired product and its regioisomer, methyl 2-(2-carbomethoxyethylthio)-3-[2-(8-phenyloctyl)phenyl]-3- hydroxypropionate. The mixture was rechromatographed on 100 grams of neutral alumina to separate the desired product.

(c) Erythro-3-(2-carboxyethylthio)-3-[2-(8-phenyloctyl)-phenyl]-2-hydroxypropanoic acid The desired product of Example 20(b) (320 mg, 0.66 mmole) was dissolved in methanol (10 ml) and stirred under argon at ice bath temperature. A 1N solution of sodium hydroxide (2.5 ml, 2.5 mmoles) was added dropwise, the ice bath removed, the mixture stirred at room temperature for 2.5 hours, and then cooled for 18 hours. After an additional 1 hour of stirring at room temperature, the methanol was stripped, the residue diluted with water and the pH adjusted to 3.5 with dilute hydrochloric acid. Extraction with ethyl acetate followed by drying over anhydrous sodium sulfate, filtration and evaporation gave the crude product which was flash chromatographed on 20 grams of silica qel eluted with 30:70:0.5 ethyl acetate:hexane:formic acid to give the free acid product.

This acid (230 mg, 0.5 mmole), under argon, was treated with a solution of potassium carbonate (276 mg, 2.0 mmoles) in water (5 ml), while stirring in an ice bath. The mixture was stirred for 10 minutes at 0° C. and then desalted on a $C_{18}$ column using about 6 column volumes of water to remove salt and excess potassium carbonate. The product was then eluted with 1:1 acetonitrile:water, the solvents evaporated and the aqueous residue lyophilized to give the dipotassium salt, hydrate.

Analysis for $C_{26}H_{34}O_5S$ 2K $H_2O$: Calculated: C, 56.49; H, 6.20; S, 5.80. Found: C, 56.12; H, 6.47; S, 5.51.

(d) 2-Hydroxy-3-[(2-carboisopropoxyethyl)thio]-3-[2-(8-phenyloctylphenyl)]propanoic acid A solution of 1 gm of 2-hydroxy-3-[(2-carboxyethyl)thio]-3-[2-(8-phenyloctyl)phenyl]propanoic acid in 10 ml isopropanol was treated with gaseous hydrogen chloride for 5 minutes. The resulting solution was stirred for an additional 5 minutes; the solvent was removed on a rotary evaporator; and the residue was taken up in methylene chloride. This solution was washed successively with water and saturated aqueous sodium chloride solution, dried over anhydrous magnesium sulfate, filtered and evaporated. Chromatography on silica gel using hexane-ethyl acetate-formic acid (65/35/0.5) gave the title compound.

ANAL:Calcd for $C_{29}H_{40}O_5S$: C, 69.87; H, 8.08; S, 6.40. Found: C, 68.76; H, 7.79; S, 6.42. 250 MHz NMR $(CDCl_3)\delta1.22$ (6H,d) 1.28–1.68 (12H,m) 2.50–2.90 (8H,m) 4.62 (1H,d) 4.72 (1H,d) 5.06 (1H, septet) 7.10–7.62 (9H,m).

EXAMPLE 21

Preparation of 2-Hydroxy-3-[(2-carbocyclopentoxyethyl)thio]-3-[2-(8-phenyloctYl)phenyl]propanoic acid.

Following the procedure of Example 20 above but substituting an equal volume of cyclopentanol for isopropanol gave the title compound. Anal.: Calcd for $C_{31}H_{42}O_5S$: C, 70.69; H, 8.04; S, 6.09. Found: C, 70.71; H, 7.67; S, 6.17. 250 MHz NMR $(CDCl_3)\delta1.28$–1.90 (20H,m) 2.49–2.91 (8H,m) 4.62 (1H,d) 4.70 (1H,d) 5.20 (1H,m) 7.10–7.63 (9H,m).

EXAMPLE 22

Preparation of 2-Hydroxy-3-[(2-carboethoxyethyl)thio]-3-[2-(8-phenyloctyl)phenyl]propanoic acid.

Following the procedure of Example 20(d) above but substitutinq an equal volume of ethanol for isopropanol gave the title compound. Anal.: Calcd for $C_{28}H_{38}O_5S$ 0.25 $H_2O$: C, 68.47; H, 7.90. Found C, 68.37; H, 7.78.

EXAMPLE 23

Preparation of 2-Hydroxy-3-[(2-carbomethoxyethyl)thio]-3-[2-(8-phenyloctyl)phenyl]propanoic acid.

A solution of methyl-3-mercaptopropionate (0.8 ml, 7.2 mmole) in tetrahydrofuran (3 ml) was added dropwise at −10° C. to a solution of n-butyllithium (3.2 ml, 2.5M in hexane) in tetrahydrofuran (10 ml) under an inert atmosphere. In a second flask, 2,3-epoxy-3-[2-(8phenyloctyl)phenyl]propanoic acid (1 gm, 2.84 mmole) was suspended in tetrahydrofuran (4 ml) and stirred at −10° C. under an inert atmosphere while a solution of titanium isopropoxide (2.2 ml, 7.15 mmole) in tetrahydrofuran (6 ml) was added dropwise keeping the internal temperature below 0° C. The resulting solution was again cooled to −10° C. and added via syringe to the above mercaptide solution, and the whole was subsequently stirred for 1 hour at 0° C. The reaction mixture was diluted with water, treated with 10% $H_2SO_4$ and extracted 3 times with ethyl acetate. The combined ethyl acetate extracts were washed with water and saturated aqueous sodium chloride solution, dried over anhydrous magnesium sulfate, filtered and evaporated. Chromatography of the residue on silica gel using hexane-ethyl acetate-formic acid (65/35/0.5) yield the title compound. Anal.: Calcd for $C_{27}H_{36}O_5S$ 0.5 $H_2O$: C, 67.33; H, 7.74. Found: C, 67.33; H, 7.46. 250 MHz NMR $(CDCl_3)\delta1.28$–1.68 (12H,m) 2.50–2.92 (8H,m) 3.70 (3H,s) 4.62 (1H,d) 4.68 (1H,d) 7.10–7.60 (9H,m).

EXAMPLE 24

Preparation of (S)-Hydroxy-3(R)-[(2-carboisopropoxyethyl) thio]-3-[2-(8-phenyloctyl)phenyl]propanoic acid.

Using the procedure outlined in Example 20 above and substituting 1 gm of the 2(S),3(R) enantiomer of 2-hydroxy-3-[(2-carboxyethyl)thio]-3-[2-(8-phenyloctyl) phenyl]propanoic acid for the racemate gave the title compound. $[a]_D$−28.38 (c 1.05, $CHCl_3$) 250 MNz NMR $(CDCl_3)\delta1.27$ (6H,d) 1.34–1.60 (12H,m) 2.50–2.92 (8H,m) 4.64 (1H,d) 4.72 (1H,d) 5.03 (1H,septet) 7.10–7.61 (9H,m). Mass Spectrum $(DCl,NH_3)$ 518 $(^{M+}+NH_4)$

EXAMPLE 25

Preparation of 2(S)-Hydroxy-3(R)-[(2-carboethoxyethyl)thio]-3-[2-(8-phenyloctyl)phenyl]propanoic acid Substituting 1 gm of the 2(S),3(R) enantiomer of 2-hydroxy-3-[(2-carboxyethyl)thio]-3-[2-(8-phenyloctyl) phenyl]propanoic acid for the racemate in Example 22 above gave the title compound. $[a]_D$−30.9° (c 1.26, $CHCl_3$).

Anal.: Calcd. for $C_{28}H_{38}O_5S$: C, 69.10; H, 7.87; S, 6.59. Found C, 68.72; H, 7.54; S, 6.70. 250 MHz NMR $(CDCl_3)\delta1.24$ (3H,t) 1.32–1.70 (12H,m) 2.50–2.90 (8H,m) 4.14 (2H,q) 4.61 (1H,d) 4.71 (1H,d) 7.10–7.60 (9H,m).

EXAMPLE 26

Preparation of Methyl-3(S)-[(2-carbomethoxyethyl)thio]-3-[2-(8-phenyloctyl)phenyl]propanoate A solution of 0.8 gm 3(S)-[(2-carboxyethyl)thio]-3-[2-(8-phenyloctyl)phenyl]propanoic acid in 10 ml methanol was treated with gaseous hydrogen chloride for 2–3 minutes. The resultinq solution was stirred for 1.5 hour at room temperature; the solvent was removed on a rotary evaporator; and the residue was taken up in methylene chloride. This solution was washed successively with water and saturated aqueous sodium chloride solution, dried over anhydrous magnesium sulfate, filtered and evaporated. The oil so obtained was dried at room temperature under 2 mm vacuum overnight to give the title compound. $[a]_D$-24.3 (c 1.0, $CHCl_3$) Anal.: Calcd. for $C_{28}H_{38}O_4S$: C, 71.61; H, 7.94; S, 6.83. Found:

C, 71.41; H, 7.77; S, 7.14 250 MHz NMR (CDCl$_3$)δ1.24–1.68 (12H,m) 2.48 (2H,t) 2.58–2.74 (6H,m) 2.91 (2H,dd) 3.62 (3H,s) 3.66 (3H,s) 4.62 (1H,t) 7.12–7.40 (9H,m).

EXAMPLE 27

Preparation of 3-[(2-carbomethoxyethyl)thio]-3-[2-(8-phenyloctyl)-phenyl]propanoic acid (a) t-Butyl 3-hydroxy-3-[2-(8-phenyloctyl) phenyl]propanoate.

A solution of diisopropylamine (4.8 ml, 0.03 mole) in tetrahydrofuran/hexane (100 ml, 1/1) was cooled to −60° C. and n-butyllithium (2.5M solution in hexane, 13.6 ml, 0.03 mole) was added. This solution was stirred for 10 minutes followed by addition of t-butyl acetate (4.6 ml, 0.03 mole). The mixture was stirred for an additional 10 minutes before addition of a solution of 2-(8-phenyloctyl)benzaldehyde (10 gm, 0.03 mole) in tetrahydrofuran (25 ml) was added dropwise. The whole was stirred first for 30 minutes at −50° C. and then for 30 minutes at −20° C. The reaction mixture was poured into aqueous acid and extracted twice with diethyl ether. The combined extracts were washed with 5% aqueous sodium bicarbonate solution and saturated aqueous sodium chloride sodium and then dried over anhydrous magnesium sulfate, filtered and evaporated. Chromatography on silica gel using hexane-ethyl acetate (95/5) to elute gave the product as an oil. 90 MHz NMR (CDCl$_3$)δ1.29–1.52 (12H,m) 2.52–2.78 (6H,m) 5.39 (1H,dd) 7.10–7.60 (9H,m).

(b) 3-[(2-carbomethoxyethyl)thio]-3-[2-(8-phenyloctyl)-phenyl]propanoic acid

A solution of t-butyl 3-hydroxy-3-[2-(8-phenyloctyl)-phenyl]propanoate (4.0 gm, 9.7 mmole) in methylene chloride (40 ml) was stirred under an inert atmosphere at −10° C. To this cold solution was added methyl 3-mercaptopropionate (6.2 ml, 56 mmole) in one portion followed by dropwise addition of trifluoroacetic acid (80 ml). The reaction mixture was then stirred for 5 hours at 0° C. Solvent and excess trifluoroacetic acid were removed on a rotary evaporator. The residue was redissolved in methylene chloride and washed twice with water and once with saturated aqueous sodium chloride solution, dried over anhydrous magnesium sulfate, filtered and evaporated. Chromatography on silica gel elutinq with hexane-ethyl acetate-formic acid (85/15/0.5) gave the title compound. Anal.: Calcd. for C$_{27}$H$_{36}$O$_4$S: C, 71.17; H, 7.74. Found: C, 70.46; H, 7.72. 250 MHz NMR (CDCl$_3$)δ1.28–1.68 (12H,m) 2.48 (2H,t) 2.56–2.72 (6H,m) 2.93 (2H,d) 3.66 (3H,s) 4.60 (1H,t) 7.18–7.39 (9H,m).

EXAMPLE 28

Preparation of 2-Hydroxy-3-[(diethylaminocarbonyl) methoxy(2-carbonylethylthio)]-3-[2-(8-phenyloctyl)-phenyl]propanoic acid.

(a) Benzhydryl 2-hydroxy-3-[(2-carboxyethyl)thio]-3-[2-(8-phenyloctyl)-phenyl]propanoate.

A partially dissolved mixture of 2-hydroxy-3-[(2-carboxyethyl)thio]-3-[2-(8-phenyloctyl)phenyl]propanoic acid prepared as in Example 20(c) (2.3 g, 5 mmol) in 25 ml of toluene was heated in an oil bath at 45° C. and stirred under argon while a solution of diphenyl-diazomethane (1.02 g, 5.26 mmol) in 25 ml of toluene was added dropwise over a period of 20 minutes. The solvent was evaporated and the residue was flash chromatographed on silica gel (30% EtOAc/hexane, 1% HCO$_2$H) to give the product.

(b) Benzhydryl 2-Hydroxy-3-[(diethylaminocarbonyl)methoxy-(2-carbonylethylthio)]-3-[2-(8-phenyloctyl)phenyl)propanoate The compound of example 28(a) (1.25 g, 2 mmol), 2-chloro-N,-N-diethylacetamide (373 mg, 2.5 mmol) and K$_2$CO$_3$ (553 mg, 4 mmol) were combined and stirred under on in 6 ml of DMF for 24 hours. The solvent was evaporated and the residue was flash chromatographed on silica gel (30–50% EtOAc/hexane) to give the product.

(c) 2-Hydroxy-3-[(diethylaminocarbonyl)methoxy(2-carbonylethylthio)]-3-[2-(8-phenyloctyl)phenyl]propanoic acid The compound of example 28(b)(600 mg, 0.8 mmol) was dissolved in 5 ml of CH$_2$Cl$_2$ and stirred under argon at 0° C. Anisole (0.15 ml) was added followed by the addition of 5 ml of trifluoroacetic acid. The reaction mixture was stirred for 10 minutes, the solvent evaporated and the residue was flash chromatographed on silica gel (50% EtOAc/hexane, 1% HCO$_2$H) to give the title compound. ANAL.:Calcd for C$_{32}$H$_{45}$O$_6$SN: C, 66.04; H, 8.05; N,2.22. Found: C,65.68; H, 7.67; N, 2.64. $^1$H NMR (250 MHZ, CDCl$_3$)δ1.2–1.7 (m, 18 H), 2.5–3.0(m,9H), 3.3(q,2H), 3.4(q,2H), 4.5–4.9(m,4H), 7.1–7.3(m,8H), 7.5–7.6(m,1H).

EXAMPLE 29

Preparation of 3-[2-(2-dimethylaminoethoxycarbonylethyl)thio]-2-hydroxy-3-[2-(8-phenyloctyl)phenyl]propanoic acid.

(a) Benzhydryl 3-[2-(2-dimethylaminoethoxycarbonylethy)thio]-2-hydroxy-3-[2-(8-phenyloctyl)phenyl)propanoic acid The compound of example 28(a)(0.5 q, 0.8 mmol) was dissolved in 15 ml of dry tetrahydrofuran and 4-methylmorpholine (0.88 ml, 8 mmol) was added. The solution was cooled to −15° C. and isobutyl chloroformate (1.04 ml, 8 mmol) added. After stirring for 1 minute, 2-dimethylaminoethanol (0.8 ml, 8 mmol) was added. After stirring for an additional 5 minutes the cooling bath was removed and the reaction stirred at room temperature for 16 hours. The reaction was filtered and the solid washed with tetrahydrofuran. The combined filtrates were evaporated and the residue chromatographed on silica gel (5%MeOH/CH$_2$Cl$_2$) to give the product.

(b) 3-[2-(2-dimethylaminoethoxycarbonylethyl)thio]-2-hydroxy-3-[2-(8-phenyloctyl)phenyl]propanoic acid.

The compound of example 29(a) was dissolved in 5 ml of CH$_2$Cl$_2$ at 0° C. while stirring under argon. Anisole (0.15 ml) was added to the reaction mixture followed by the addition of 5 ml of trifluoroacetic acid. After stirring for an additional 10 minutes, the solution was evaporated, the residue dissolved in CH$_2$Cl$_2$, washed with water, the organic phase dried over anhydrous MgSO$_4$, filtered and evaporated. The residue was purified by silica gel thin layer chromatography (15% MEOH/CH$_2$Cl$_2$, 0.5% HCO$_2$H) to give the title compound.

$^1$H NMR (250 MHZ, CDCl$_3$)δ1.2–1.7 (m,12H). 2.5–3.4 (m,16H), 4.1–4.5(m,2H), 7.1–7.5(m,9H).

EXAMPLE 30

As a specific embodiment of a composition of this invention, a precursor, such as the compound of Example 20, 21, 22 or 23 is dissolved in 25 mM sodium carbonate at a concentration of 0.4 percent and aerosolized from a nebulizer operating at an air flow adjusted to deliver the desired aerosolized weight of drug.

EXAMPLE 31

As an additional specific embodiment of a composition of this invention, the compound of Example 25or 28 is admixed with a propellant (98.9%) and a surfactant (1%) at a concentration of 0.1% and administered from a powder inhalation device adjusted to deliver the desired weight of drug.

What is claimed:

1. A compound represented by the following structural formula (I):

wherein
(a) R$_1$ is C$_8$ alkyl, C$_1$ to C$_{12}$ alkoxy, C$_7$ to C$_{12}$ alkylthio. C$_{10}$ to C$_{12}$ 1-alkynyl, 10-undecynyloxy, 11-dodecynyl, phenyl-C$_4$ to C$_{10}$ alkyl, phenyl-C$_3$ to C$_9$ alkoxy, phenylthio-C$_3$ to C$_9$ alkyl with the phenyl optionally mono substituted with bromo, chloro, trifluoromethyl, methylthio or trifluoromethylthio, thienyl-C$_4$ to C$_{10}$ alkyl, furyl-C$_4$ to C$_{10}$ alkyl, trifluoromethyl-C$_7$ to C$_{12}$ alkyl or cyclohexyl C$_4$ to C$_{10}$ alkyl; and R$_2$ is hydrogen, bromo, chloro, methyl, trifluoromethyl, hydroxy, C$_1$ to C$_4$ alkoxy or nitro; (b) or R$_1$ is hydrogen and R$_2$ is C$_8$ to C$_{13}$ alkyl, C$_1$ to C$_{12}$ alkoxy, C$_7$ to C$_{12}$ alkylthio, C$_{10}$ to C$_{12}$ 1-alkynyl, 10-undecynyloxy, 11-dodecynyl, phenyl-C$_4$ to C$_{10}$ alkyl, phenyl-C$_3$ to C$_9$ alkoxy, phenylthio-C$_3$ to C$_9$ alkyl with the phenyl optionally mono substituted with bromo, chloro, trifluoromethyl, methylthio or trifluoromethylthio, furyl-C$_4$ to C$_{10}$ alkyl, trifluoromethyl-C$_7$ to C$_{12}$ alkyl or cyclohexyl-C$_4$ to C$_{10}$ alkyl;

q is 0, 1, or 2;
Y is COR$_3$

CH(CH$_2$)$_m$COR$_3$ or CH(CH$_2$)$_m$—C-tetrazol-5-yl;
|                                 |
R$_4$                              R$_4$ wherein the tetrazol-5-yl is unsubstituted or substituted with A;
A is R$_{16}$
|
(C)$_j$—R$_{18}$;
|
R$_{17}$ R$_{16}$ and R$_{17}$ are independently hydrogen or C$_{1-4}$ alkyl;
j is 0 to 6;
R$_{18}$ is hydrogen, C$_{1-4}$alkyl, COR$_3$, SO$_3$H, SO$_2$NH$_2$, COCH$_2$OH or CHOHCH$_2$OH;
R$_3$ is amino, (CH$_2$)$_n$CO$_2$CH$_2$CONR$_{16}$R$_{17}$, or OR$_{14}$;
R$_{14}$ is hydrogen, C$_1$ to C$_6$ alkyl, cycloalkyl, aryl, arylalkyl, alkylaryl, alkylarylalkyl, alkyl substituted amino or aklylamino, OCH$_2$CONR$_7$R$_8$, indanyl, pivaloxyloxymethyl, acetoxymethyl, propionyloxymethyl, glycyloxymethyl, phenylglycyloxymethyl, or thienylglycyloxymethyl;
R$_4$ is hydrogen, methyl, C$_1$ to C$_4$ alkoxy, fluoro or hydroxy;
m is 0, or 1;
R is (CH$_2$)$_n$C(R$_5$)(H)COR$_6$, CH(CO$_2$H)CH$_2$COR$_6$, (CH$_2$)$_n$CO$_2$CH$_2$CONR$_{16}$R$_{17}$, or n is 0 to 6;
R$_5$ is hydrogen, amino, or NHCOCH$_2$CH$_2$CH(NH$_2$)CO$_2$H;
R$_6$ is amino, NH(CH$_2$)$_n$CO$_2$H, SO$_3$H, SO$_2$NH$_2$, CN, tetrazol-5-yl unsubstituted or substituted with A as defined above, or OR$_{15}$;
R$_7$ is hydrogen, C$_1$ to C$_4$ alkyl or C$_3$ to C$_4$ alkenyl;
R$_8$ is hydrogen, C$_1$ to C$_4$ alkyl, carboxyl or carboxamido, or, when R$_7$ and R$_9$ are hydrogen or C$_1$ to C$_4$ alkyl, (CH$_2$)$_m$COOR$_{15}$;
R$_9$ is hydrogen, C$_1$ to C$_4$ allkyl or (CH$_2$)$_m$COOR$_{15}$;
R$_{15}$ is hydrogen, C$_1$ to C$_6$ alkyl, cycloalkyl, aryl, arylalkyl, alkylaryl, alkylarylalkyl, allayl substituted amino or alkylamino, COH$_2$CONR$_7$R$_8$, indanyl, pivaloxyloxymethyl, acetoxymethyl, propionyloxymethyl, glycyloxymethyl, phenylglycyloxymethyl, or thienylglycyloxymethyl;
provided that (1) when n is 0, R$_5$ is hydrogen, (2) R$_7$, R$_8$ and R$_9$ are not all hydrogen, (3) any of R$_1$ and R$_2$ above are not alkylthio or phenylthioalkyl when q is 1 or 2, (4) R$_3$ and R$_6$ are not both hydroxy, (5) OR$_{14}$ and OR$_{15}$ are not simultaneously hydroxy; (6) if R$_4$ is hydroxy and m is 0, R$_{14}$ is hydrogen; and at least one of Y or R contains a terminal ester group; or
a pharmaceutically acceptable salt thereof.

2. A compound according to claim 1 wherein R$_3$ is amino or OR$_{14}$ where R$_{14}$ is hydrogen or C$_1$ to C$_6$ alkyl and R$_4$ is amino or OR$_{15}$ where R$_{15}$ is hydrogen or C$_1$ to C$_6$ alkyl.

3. A compound according to claim 1 wherein R$_4$ is hydroxy, m is 0 and R$_{15}$ is not hydrogen.

4. A compound of claim 3 represented by structural formula (IIA)

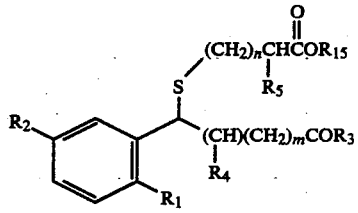

where R₄ is hydroxy; m is 0; R₃ is amino or OH; and R₁₅ is other than hydrogen.

5. A compound of claim 4 which is:
2-hydroxy-3-[2-carboisopropoxyethyl)thio]-3-[2-(8-phenyloctyl)]propanoic acid;
2-hydroxy-3-[(2-carbocyclopentoxyethyl)thio]-3-[2-(8-phenyloctyl)phenyl]propanoic acid;
2-hydroxy-3-[2-carboethoxyethyl)thio]-3-[2-(8-phenyloctyl)phenyl]propanoic acid;
2(S)-hydroxy-3(R)-[(2-carboisopropoxyethyl)thio]-3-[2-(8-phenyloctyl)phenyl]propanoic acid;
2(S)-hydroxy-3(R)-[(2-carboethoxyethyl)thio]-3-[2-(8-phenyloctyl)phenyl]propanoic acid;
2-hydroxy-3-[(2-carbomethoxyethyl)thio]-3-[2-(8-phenyloctyl)phenyl]propanoic acid;
2-hydroxy-3-[(diethylaminocarbonyl)methoxy (2-carbonylethylthio)]-3-[2-(8-phenyloctyl)phenyl]propanoic acid; or
3-[2-(2-dimethylaminoethoxycarbonylethyl)thio]-2-hydroxy-3-[2-(8-phenyloctyl)phenyl]propanoic acid.

6. A compound of claim 2 represented by structural formula (III)

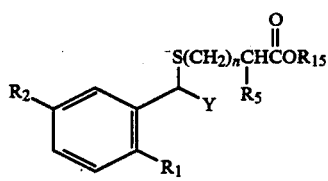

wherein R₄ is other than hydroxy R₄ is hydrogen; and R₁₅ is other than hydrogen.

7. A compound of claim 6 which is:
methyl 4-thia-5-(2-dodecylphenyl)-5-tetrazol-5-yl)pentanoate;
methyl 4-thia-5-(2-dodecylphenyl)-5-carboxamidopentanoate;
methyl 4-thia-5-(2-dodecylphenyl)-6-(tetrazol-5-yl)hexanoate; or
3-[(2-carbomethoxyethyl)thio]-3-[2-(8-phenyloctyl)phenyl]propanoic acid.

8. A compound of claim 2 represented by structural formula (IVA)

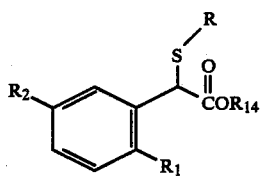

wherein R₁₅ is hydrogen; and R₁₄ is other than hydrogen.

9. A compound of claim 8 which is
methyl 2-(3-carboxypropylthio)-2-(2-dodecylphenyl)acetate;
methyl 2-(2-carboxamidoethylthio)-2-(2-dodecylphenyl)acetate;
methyl 2-(2-dodecylphenyl)-5-sulfo-3-thiapentanoate;
5-carbomethoxy-5-(2-dodecylphenyl)-3-carboxy-4-thiapentanoic acid;
methyl 2-(2-sulfonamidoethylthio)-2-(2-dodecylphenyl)acetate; or
methyl 2-(2-cyanoethylthio)-2-(2-dodecylphenyl)acetate.

10. A compound of claim 2 represented by structural formula (IVB)

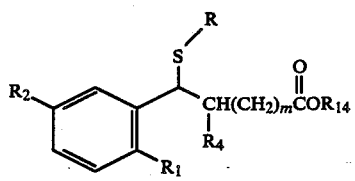

wherein R₄ is not hydroxy when m is 0, R₁₅ is hydrogen, and R₁₄ is other than hydrogen.

11. A compound of claim 10 which is:
t-butyl 3-(2-carboxyethylthio)-3-(2-dodecylphenyl)propionate;
methyl 2-methyl-3-(2-carboxyethylthio)-3-(2-dodecylphenyl)propanoate; or
t-butyl 3-(2-carboxyethylthio)-3-[2-(8-phenyloctyl)-5-trifluoromethylphenyl]propanoate;

12. A compound of claim 2 represented by structural formula (VA)

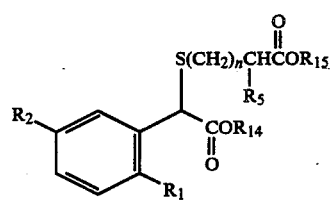

wherein R₄ is not hydroxy when m is 0, and R₁₄ and R₁₅ are other than hydrogen.

13. A compound of claim 12 which is:
methyl 2-(carbomethoxymethylthio)-2-(2-dodecylphenyl)acetate;
methyl 2-(2-carbomethoxyethylthio)-2-(2-dodecylphenyl)acetate;
3-aza-4-oxo-7-thia-8-(2-dodecylphenyl)nonanedioic acid dimethyl ester;
methyl 2-(2-carbomethoxyethylthio)-2-[2-(8-phenyloctyl)phenyl]acetate; or
di-(5-butyl)-3-aza-4-oxo-7-thia-8-(2-dodecylphenyl)decanedioate.

14. A COmpound of claim 2 represented by structural formula (VB)

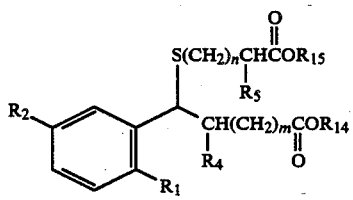

wherein R₄ is not hydroxy when m is 0, and R₁₄ and R₁₅ are other than hydrogen.

15. A compound of claim 14 which is:
methyl 3(S)-[(2-carbomethoxyethyl)thio]-3-[2-(8-phenyloctyl)phenyl]propanoate; di-(t-butyl)-3-aza-4-oxo-7-thia-8-(2-dodecylphenyl)decanedioate; or methyl 3-[(2-carbomethoxyethyl)thio]-3-[2-(8-phenyloctyl)phenyl]propanoate.

16. A compound of claim 1 having the structural formula (VC)

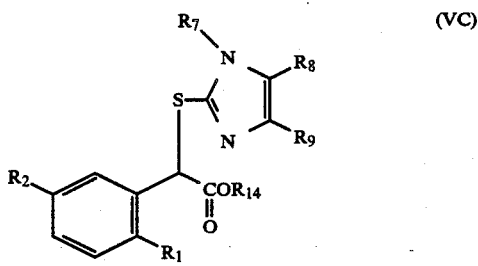

wherein one of R₈ or R₉ is

and R₁₅ is other than hydrogen.

17. A compound of claim 16 which is:
methyl 2-(2-dodecylphenyl)-2-(1,4-dimethyl-5-carbethoxy-2-imidazolylthio)acetate; or
methyl 2-(2-dodecylphenyl)-2-(1-methyl-4-propyl-5-carbethoxy-2-imidazolylthio)acetate.

18. A pharmaceutical composition for inhibiting the effects of leukotriene comprising a pharmaceutical carrier or diluent and a nontoxic amount sufficient to produce said inhibition of a compound of claim 2, formula (I).

19. A pharmaceutical composition according to claim 2 in a form suitable for administration by inhalation, parenteral administration, oral administration, or topical administration.

20. A pharmaceutical composition according to claim 19 in which the active ingredient is 2-hydroxy-3-carbomethoxyethylthio)-3-[2-(8-phenyloctyl)phenyl]-propanoic acid or a pharmaceutically acceptable salt thereof.

21. A pharmaceutical composition for inhibiting antigen-induced respiratory anaphylaxis comprising a pharmaceutical carrier or diluent and nontoxic amounts sufficient to produce said inhibition of a compound of claim 2, formula (I), and an histamine H₁-receptor antagonist.

22. A pharmaceutical composition according to claim 21 in which the active ingredients are 2-hydroxy-3-(2-carbomethoxyethylthio)-3-[2-(8-phenyloctyl)-phenyl]-propanoic acid, or a pharmaceutically acceptable salt thereof, and 2-[4-(5-bromo-3-methylpyrid-2-yl)butylamino]5-[(6-methylpyrid-3-yl)methyl]4-pyrimidone.

23. A method of treating a pulmonary disease in which leukotrienes are a factor in a subject in need thereof comprising administration to such subject an effective amount of a compound of claim 1.

24. A method of treating a non-pulmonary disease in which leukotrienes are a factor in a subject in need thereof comprising administration to such subject an effective amount of a compound of claim 2.

25. A method of treating a pulmonary or non-pulmonary disease in which leukotrienes are a factor in a subject in need thereof comprising administration to such subject an effective amount of a composition of claim 18.

26. A method of treating a pulmonary or non-pulmonary disease in which leukotrienes are a factor in a subject in need thereof comprising administration to such subject an effective amount of a composition of claim 21.

* * * * *

UNITED STATES PATENT AND TRADEMARK OFFICE
CERTIFICATE OF CORRECTION

PATENT NO. : 4,937,253

DATED : Jun. 26, 1990

INVENTOR(S) : Gleason, et al.

Page 1 of 5

It is certified that error appears in the above-identified patent and that said Letters Patent is hereby corrected as shown below:

Column 1, line 5: "No. b" should be -- No. --

Column 2, line 54: "areas" should be -- areas. --

Column 6, line 13: "$(CH_2)_n COCOR_6$," should be -- $(CH_2)_n CHCOR_6$, --

Column 16, line 25: "of fom-" should be -- of for- --

Column 18, line 55: "2-(carbomethoxymethylthio)-2-(2decylphenyl-" should be -- 2-(Carbomethoxymethylthio)-2-(2-decylphenyl- --

Column 18, line 57: "2-(Carbomethoxymethylthio)-2-(2octylphenyl-" should be -- 2-(Carbomethoxymethylthio)-2-(2-octylphenyl- --

Column 18, line 62: "2-(2-carbomethoxyethylthio)-2(2-dodecylphenyl)ace-" should be -- 2-(2-carbomethoxyethylthio)-2-(2-dodecylphenyl)ace- --

Column 19, line 11: "2-(2-dodecylphenyl)-2(1,4-dimethyl-5-carbethoxy-2-" should be -- 2-(2-dodecylphenyl)-2-(1,4-dimethyl-5-carbethoxy-2- --

Column 19, line 29: "2-(2-Dodecylphenyl)-2-(1-ethyl-5-carbox-" should be -- 2-(2-Dodecylphenyl)-2-(1-methyl-5-carbox- --

Column 19, line 40: "3-Aza-4-oxo-7-thia-8-(2-dodecyphenyl)nonanedioic" should be -- 3-Aza-4-oxo-7-thia-8-(2-dodecylphenyl)nonanedioic --

Column 19, line 48: "silica el" should be -- silica gel --

Column 19, line 68: "(m.6H). 1.1-1.9(m.27H)." should be -- (m.6H), 1.1-1.9(m.27H), --

UNITED STATES PATENT AND TRADEMARK OFFICE
CERTIFICATE OF CORRECTION

PATENT NO. : 4,937,253

DATED : Jun. 26, 1990

INVENTOR(S) : Gleason, et al.

Page 2 of 5

It is certified that error appears in the above-identified patent and that said Letters Patent is hereby corrected as shown below:

Column 20, line 1: "2.6(s.3H). 3.7(s.3H). 4.25(q.2H). 5.8(s.1H)." should be -- 2.6(s,3H), 3.7(s,3H), 4.25(q,2H), 5.8(s,1H), --

Column 20, line 2: "7.1-7.2(m.3H)." should be -- 7.1-7.2(m,3H), --

Column 20, line 17: "CDC13" should be -- $CDCl_3$ --

Column 20, line 35: "resultinq" should be -- resulting --

Column 21, line 28: "phenyl1,7-octadiynyl)benzaldehyde." should be -- phenyl-1,7-octadiynyl)benzaldehyde. --

Column 21, line 34: "qive" should be -- give --

Column 21, line 40: "at ° C." should be -- at 0° C. --

Column 22, line 11: "qive" should be -- give --

Column 22, line 42: "qive" should be -- give --

Column 23, line 1: "tinq" should be -- ting --

Column 23, line 17: "resultinq" should be -- resulting --

Column 23, line 41: "2-methyl-3-(2-carboxyethylthio)-3(2-dodecylphenyl)-" should be -- 2-methyl-3-(2-carboxyethylthio)-3-(2-dodecylphenyl)- --

Column 23, line 65: "resultinq" should be -- resulting --

Column 24, line 27: "Hq." should be -- Hg. --

Column 24, line 48: "(20 q)" should be -- (20 g) --

UNITED STATES PATENT AND TRADEMARK OFFICE
CERTIFICATE OF CORRECTION

PATENT NO. : 4,937,253
DATED : Jun. 26, 1990
INVENTOR(S) : Gleason, et al.

It is certified that error appears in the above-identified patent and that said Letters Patent is hereby corrected as shown below:

Column 26, line 15: "(11.7 q," should be -- (11.7 g, --

Column 26, line 61: "elutinq" should be -- eluting --

Column 27, line 31: "5.0 q," should be -- 5.0 g, --

Column 27, line 35: "thoxyethyl-ptoluenethiosulfonate" should be -- thoxyethyl-p-toluenethiosulfonate --

Column 27, line 38: "23° C. acidified" should be -- 23° C., acidified --

Column 27, line 44: "qive" should be -- give --

Column 28, line 25: "(0.99 q," should be -- (0.99 g, --

Column 28, line 27: "15 8 mmoles)" should be -- 15.8 mmoles) --

Column 28, line 28: "0.59 q," -- should be -- (0.59 g, --

Column 29, line 6: "to qive" should be -- to give --

Column 29, line 15: "2-(tetrazol-5-yl)-2((2-dodecylbenzoyl) acetate" should be -- 2-(tetrazol-5-yl)-2-(2-dodecylbenzoyl) acetate --

Column 29, line 26: "(4.06 q," should be -- (4.06 g, --

Column 29, line 46: "to qive" should be -- to give --

Column 30, line 2: "3 52(d,2H)," should be -- 3.52(d,2H), --

Column 30, line 24: "(2.94 q," should be -- (2.94 g, --

UNITED STATES PATENT AND TRADEMARK OFFICE
CERTIFICATE OF CORRECTION

PATENT NO. : 4,937,253

DATED : Jun. 26, 1990

INVENTOR(S) : Gleason, et al.

It is certified that error appears in the above-identified patent and that said Letters Patent is hereby corrected as shown below:

Column 30, line 37: "phenyl]-2-hydroxypropanoate" should be -- phenyl]-2-hydroxypropionate --

Column 31, line 20: "qaseous" should be -- gaseous --

Column 31, line 54: "substitutinq" should be -- substituting --

Column 31, line 67: "(8phenyloctyl)phenyl]propanoic" should be -- (8-phenyloctyl)phenyl]propanoic --

Column 32, line 34: "($^{M+}$ +$NH_4$)" should be -- ($M^+$ +$NH_4$) --

Column 32, line 59: "resultinq" should be -- resulting --

Column 33, line 49: "elutinq" should be -- eluting --

Column 34, line 14: "under on" should be -- under argon --

Column 34, line 44: "28(a)(0.5 q,)" should be -- 28(a)(0.5 g,) --

Column 35, line 18: "Example 25or" should be -- Example 25 or --

Column 36, line 15: "$OCH_2CONR_7R_8$," should be -- -$OCH_2CONR_7R_8$, --

Column 36, line 47: "pivaloxyloxymethyl," should be -- pivaloyloxymethyl, --

UNITED STATES PATENT AND TRADEMARK OFFICE
CERTIFICATE OF CORRECTION

PATENT NO. : 4,937,253

DATED : Jun. 26, 1990

INVENTOR(S) : Gleason, et al.

It is certified that error appears in the above-identified patent and that said Letters Patent is hereby corrected as shown below:

Column 37, line 57: "A COmpound" should be -- A compound --

Column 39, line 23: "Rjis" should be -- $R_9$ is --

Signed and Sealed this

Twenty-third Day of June, 1992

Attest:

DOUGLAS B. COMER

Attesting Officer

Acting Commissioner of Patents and Trademarks